(12) United States Patent
Davies et al.

(10) Patent No.: US 10,093,609 B2
(45) Date of Patent: Oct. 9, 2018

(54) TAK1 KINASE INHIBITORS, COMPOSITIONS, AND USES RELATED THERETO

(71) Applicant: Emory University, Atlanta, GA (US)

(72) Inventors: Huw M. L. Davies, Duluth, GA (US); Spandan Chennamadhavuni, Natick, MA (US); Andrei Bakin, Buffalo, NY (US)

(73) Assignee: Emory University, Atlanta, GA (US)

( * ) Notice: Subject to any disclaimer, the term of this patent is extended or adjusted under 35 U.S.C. 154(b) by 0 days.

(21) Appl. No.: 15/694,982

(22) Filed: Sep. 4, 2017

(65) Prior Publication Data

US 2017/0369417 A1  Dec. 28, 2017

Related U.S. Application Data

(62) Division of application No. 14/234,127, filed as application No. PCT/US2012/047314 on Jul. 19, 2012, now Pat. No. 9,751,825.

(60) Provisional application No. 61/509,161, filed on Jul. 19, 2011.

(51) Int. Cl.
| | |
|---|---|
| *A61K 31/216* | (2006.01) |
| *A61K 31/194* | (2006.01) |
| *C07C 69/73* | (2006.01) |
| *C07C 259/06* | (2006.01) |
| *C07C 69/736* | (2006.01) |
| *C07C 67/31* | (2006.01) |
| *C07C 57/42* | (2006.01) |
| *C07C 51/00* | (2006.01) |
| *A61K 31/405* | (2006.01) |
| *A61K 31/36* | (2006.01) |
| *A61K 31/357* | (2006.01) |
| *A61K 31/343* | (2006.01) |
| *C07D 307/80* | (2006.01) |
| *C07D 209/24* | (2006.01) |
| *C07C 201/12* | (2006.01) |
| *C07C 69/604* | (2006.01) |
| *C07C 69/618* | (2006.01) |
| *C07C 69/65* | (2006.01) |
| *C07C 69/732* | (2006.01) |
| *C07C 69/734* | (2006.01) |
| *C07C 69/738* | (2006.01) |
| *C07D 317/60* | (2006.01) |
| *C07D 319/18* | (2006.01) |
| *C07D 209/26* | (2006.01) |
| *C07D 209/34* | (2006.01) |
| *C07D 307/79* | (2006.01) |
| *C07C 205/56* | (2006.01) |
| *C07D 317/68* | (2006.01) |

(52) U.S. Cl.
CPC ............ *C07C 69/73* (2013.01); *A61K 31/194* (2013.01); *A61K 31/216* (2013.01); *A61K 31/343* (2013.01); *A61K 31/357* (2013.01); *A61K 31/36* (2013.01); *A61K 31/405* (2013.01); *C07C 51/00* (2013.01); *C07C 57/42* (2013.01); *C07C 67/31* (2013.01); *C07C 69/604* (2013.01); *C07C 69/618* (2013.01); *C07C 69/65* (2013.01); *C07C 69/732* (2013.01); *C07C 69/734* (2013.01); *C07C 69/736* (2013.01); *C07C 69/738* (2013.01); *C07C 201/12* (2013.01); *C07C 205/56* (2013.01); *C07C 259/06* (2013.01); *C07D 209/24* (2013.01); *C07D 209/26* (2013.01); *C07D 209/34* (2013.01); *C07D 307/79* (2013.01); *C07D 307/80* (2013.01); *C07D 317/60* (2013.01); *C07D 317/68* (2013.01); *C07D 319/18* (2013.01)

(58) Field of Classification Search
None
See application file for complete search history.

(56) References Cited

U.S. PATENT DOCUMENTS

| | | | |
|---|---|---|---|
| 2,852,556 | A | 9/1958 | Katz |
| 2,913,450 | A | 11/1959 | Katz |
| 4,886,835 | A | 12/1989 | Malleron |
| 2006/0079494 | A1 | 4/2006 | Santi |
| 2009/0312396 | A1 | 12/2009 | Byth |

FOREIGN PATENT DOCUMENTS

JP  2003261508  9/2003

OTHER PUBLICATIONS

Bernard et al. Efect of Covalent TAK1 Inhibitors on the Viability of Pancreatic, Renal and Colon Cancer Cells, Biochemistry and Molecular Biology, 2016, Abst 650.2.
Buglio et al. Essential role of TAK1 in regulating mantle cell lymphoma survival, Blood. 2012;120(2): 347-355.
Cai et al. Elevated TAK1 augments tumor growth and metastatic capacities of ovarian cancer cells through activation of NF-κB signaling, Oncotarget, vol. 5, No. 17, 7549.

(Continued)

*Primary Examiner* — Samantha L Shterengarts
(74) *Attorney, Agent, or Firm* — Emory Patent Group

(57) ABSTRACT

The disclosure relates to TAK1 inhibitors, compositions, and uses related thereto. In certain embodiments, the disclosure relates to compounds of formula I, pharmaceutical compositions having a compound of formula I, and methods of treating or preventing cancer by administering an effective amount of a pharmaceutical composition having a compound of formula I to a subject in need thereof.

17 Claims, 4 Drawing Sheets

(56) References Cited

OTHER PUBLICATIONS

Coda et al. Copper(II) in organic synthesis. VII reaction of the copper(II) acetate complex of 1-methylisatin-3-chlorophenylhydrazone with dimethyl acetylenedicarboxylate, Tetrahedron, vol. 43, Issue 12, 1987, pp. 2843-2852.
Davies Intermolecular reactions of electron-rich heterocycles with copper and rhodium carbenoids, Chem. Soc. Rev., 2007, 36, 1109-1119.
Fan et al. TAK1 inhibitor 5Z-7-oxozeaenol sensitizes neuroblastoma to chemotherapy, Apoptosis (2013) 18:1224-1234.
Guan et al. TAK1 inhibitor 5Z-7-oxozeaenol sensitizes cervical cancer to doxorubicin-induced apoptosis. Oncotarget, 2017, vol. 8, (No. 20), pp: 33666-33675.
Hahn et al., Efficient and regioselective chromium(0)-catalyzed reaction of 2-substituted furans with diazo compounds: stereoselective synthesis of (2E,4Z)-2-aryl-hexadienedioic acid diestersJournal of Organometallic Chemistry, (2004), 689(16), 2662-2673.
Hedley et al. Investigation into Factors Influencing Stereoselectivity in the Reactions of Heterocycles with Donor-Acceptor-Substituted Rhodium Carbenoids, J. Org. Chem., 2006, 71 (14), pp. 5349-5356.
Lin et al. The role of TAK1 expression in thyroid cancer, Int J Clin Exp Pathol 2015;8(11):14449-14456.
Malleron et al. Penta- and hexadienoic acid derivatives: a novel series of 5-lipoxygenase inhibitors, J. Med. Chem., 1990, 33 (10), pp. 2744-2749.
Mittal et al., Synthesis of leprapinic acid and constitution of pinastric acid, J. Chem. Soc., 1956, 1734-1735.
Miyauchi et al. Rhodium-Catalyzed Intermolecular [2+2+2] Cross-Trimerization of Aryl Ethynyl Ethers and Carbonyl compounds to Produce Dienyl Esters, Angewandte Chemie, International Edition (2011), 50(46), 10922-10926.
Ninomiya et al. A resorcylic acid lactone, 5Z-7-oxozeaenol, prevents inflammation by inhibiting the catalytic activity of TAK1 MAPK kinase kinase, J Biol Chem. May 16, 2003;278(20):18485-90.
Pirrung et al. Dipolar cycloaddition of cyclic rhodium carbenoids to aromatic heterocycles, J. Org. Chem., 1991, 56 (22), pp. 6269-6271.
Safina et al. TAK1 is required for TGF-β1-mediated regulation of matrix metalloproteinase-9 and metastasis, Oncogene (2008) 27, 1198-1207.
Shirakawa et al. Palladium-Catalyzed Dimerization-Carbostannylation of Alkynes: Synthesis of Highly Conjugated Alkenylstannanes, J. Am. Chem. Soc., 1999, 121 (17), pp. 4290-4291.
Sietmann et al. Novel ring cleavage products in the biotransformation of biphenyl by the yeast *Trichosporon mucoides*, Appl Environ Microbiol. Sep. 2001;67(9):4158-65.
Sietmann et al. Oxidative ring cleavage of low chlorinated biphenyl derivatives by fungi leads to the formation of chlorinated lactone derivatives. Chemosphere. 2006, 64(4):672-85.
Tenshin et al. TAK1 inhibition subverts the osteoclastogenic action of TRAIL while potentiating its antimyeloma effects, Blood Advances, 2017, vol. 1, No. 24, 2124-2137.
Van Belzen et al. Stoichiometric and Catalytic Conversion of Alkynes to Conjugated (Z,Z)-Dienes and Cyclopentadienes via Palladacyclopentadienes and 1,3-Dienylpalladium(II) Halide and Triorganopalladium(IV) Halide Compounds Containing Chelating Nitrogen Ligands, Organometallics 1998, 17, 1812-1825.
USP 37, General Information / 1231 Water for Pharmaceutical Purposes 1.
Zhao et al. MicroRNA-26b suppresses the NF-κB signaling and enhances the chemosensitivity of hepatocellular carcinoma cells by targeting TAK1 and TAB3, Molecular Cancer 2014, 13:35.

TAK1 KINASE INHIBITORS, COMPOSITIONS, AND USES RELATED THERETO

CROSS REFERENCE TO RELATED APPLICATIONS

This application is a division of U.S. application Ser. No. 14/234,127 filed Apr. 10, 2014, which is the National Stage of International Application No. PCT/US2012/047314 filed Jul. 19, 2012, which claims the benefit of U.S. Provisional Application No. 61/509,161 filed Jul. 19, 2011. The entirety of each of these applications is hereby incorporated by reference for all purposes.

STATEMENT REGARDING FEDERALLY FUNDED RESEARCH

This invention was made with government support under Grant No. CA159133 awarded by the National Institutes of Health. The government has certain rights in the invention.

FIELD

The disclosure relates to TAK1 inhibitors, compositions, and uses related thereto. In certain embodiments, the disclosure relates to compounds of formula I, pharmaceutical compositions having a compound of formula I, and methods of treating or preventing cancer by administering an effective amount of a pharmaceutical composition having a compound of formula I to a subject in need thereof.

BACKGROUND

According to the American Cancer Society, about 1,529,560 new cancer cases are expected to be diagnosed in 2010 in the United States alone. Cancer is a condition where cell growth regulators do not function properly. As a result, cell growth exceeds cell death. Transforming Growth Factor-β-Activated Kinase 1 (TAK1) inhibition is a mechanism to down-regulate cancer growth. Transforming growth factor-β1 (TGF-β1) cytokine regulates the composition of extracellular matrix (ECM), matrix proteolysis, and inflammatory responses. TGF-β1 suppresses tumor growth at early stages of cancer, whereas, at late stages, TGF-β1 promotes tumor spreading by through angiogenesis. Interference with TGF-β-activated protein kinase 1 (TAK1) activity alters TGF-β interactions with MMP-9 and the metastatic potential of cancer cells. See Safina et al., Oncogene 2008, 27, 1198-1207 (experiments showing that TAK1 RNA interference (siRNA) reduces expression of MMP-9 and tumor cell invasion). Thus, there is a need to identify improved TAK1 inhibitors useful in cancer treatments.

Hahn et al., Journal of Organometallic Chemistry, (2004), 689(16), 2662-2673, disclose the catalyzed reaction of 2-substituted furans with diazo compounds provides (2E, 4Z)-2-arylhexadienedioic acid diesters. See also Hedley et al., J. Org. Chem., 2006, 71 (14), 5349-5356.

SUMMARY

It has been discovered that certain diene compounds are TAK1 inhibitors. In certain embodiments, the disclosure relates to compounds of formula I, pharmaceutical compositions having a compound of formula I, and methods of treating or preventing cancer by administering a pharmaceutical composition or pharmaceutically acceptable salt thereof having a compound of formula I to a subject in need thereof.

In certain embodiments, the disclosure relates to compounds of formula I,

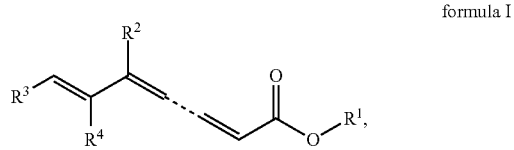

formula I or salts of prodrugs thereof wherein is a single bond with a trans isomer to $R^2$ and a cis isomer to $-(C=O)R^1$, a cis isomer to $R^2$ and a cis isomer to $-(C=O)R^1$; or a trans isomer to $R^2$ and a trans isomer to $-(C=O)R^1$;

$R^1$ is hydrogen, hydroxy, alkyl, alkoxy, carbocyclyl, aryl, or heterocyclyl, wherein $R^1$ is optionally substituted with one or more, the same or different, $R^{10}$;

$R^2$ is formyl, carboxy, carbamoyl, or phosphonate, wherein $R^2$ is optionally substituted with one or more, the same or different, $R^{10}$;

$R^3$ is nitro, cyano, hydroxy, amino, mercapto, formyl, carboxy, carbamoyl, alkylamino, (alkyl)$_2$amino, alkylsulfinyl, alkylsulfonyl, arylsulfonyl, aryl, or heteroaryl wherein $R^3$ is optionally substituted with one or more, the same or different, $R^{10}$;

$R^4$ is hydrogen or $R^3$ and $R^4$ and the attached atoms form an aryl or heteroaryl ring wherein the ring is optionally substituted with one or more, the same or different, $R^{10}$;

$R^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{10}$ is optionally substituted with one or more, the same or different, $R^{11}$;

$R^{11}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{11}$ is optionally substituted with one or more, the same or different, $R^{12}$;

$R^{12}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{12}$ is optionally substituted with one or more, the same or different, $R^{13}$; and $R^{13}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethyl sulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, the disclosure relates to the use of a compound as described herein in the production of a medicament for the treatment cancer. Compounds disclosed here can be contained in pharmaceutical compositions and administered alone or in combination with one or more additional active agents. The active agents can be administered simultaneously in the same dosage form or in separate dosage forms. Alternatively, the active agents can be administered sequentially in different dosage forms.

In certain embodiments, the disclosure relates to methods of treating cancer comprising administering a compound disclosed herein in combination with TNF-alpha or TNF-related apoptosis-inducing ligand (TRAIL) or related polypeptide.

The compound can be combined with one or more pharmaceutically acceptable excipients to form a pharmaceutical composition. The compositions can be formulated for enteral, parenteral, topical, transdermal, or pulmonary administration. The compounds can be formulated for immediate release, controlled release, and combinations thereof.

In certain embodiments, the disclosure relates to method of making compounds disclosed herein by mixing starting materials and reagents disclosed herein under conditions such that the compounds are formed. In certain embodiments, the disclosure relates to methods of preparing compounds disclosed herein by mixing a compound with a diazo group with furan under conditions such that an alpha, beta unsaturated ester or ketone is formed in the presence of a metal catalyst such as $Rh_2(OAc)_4$.

DETAILED DESCRIPTION

Figure 1A:
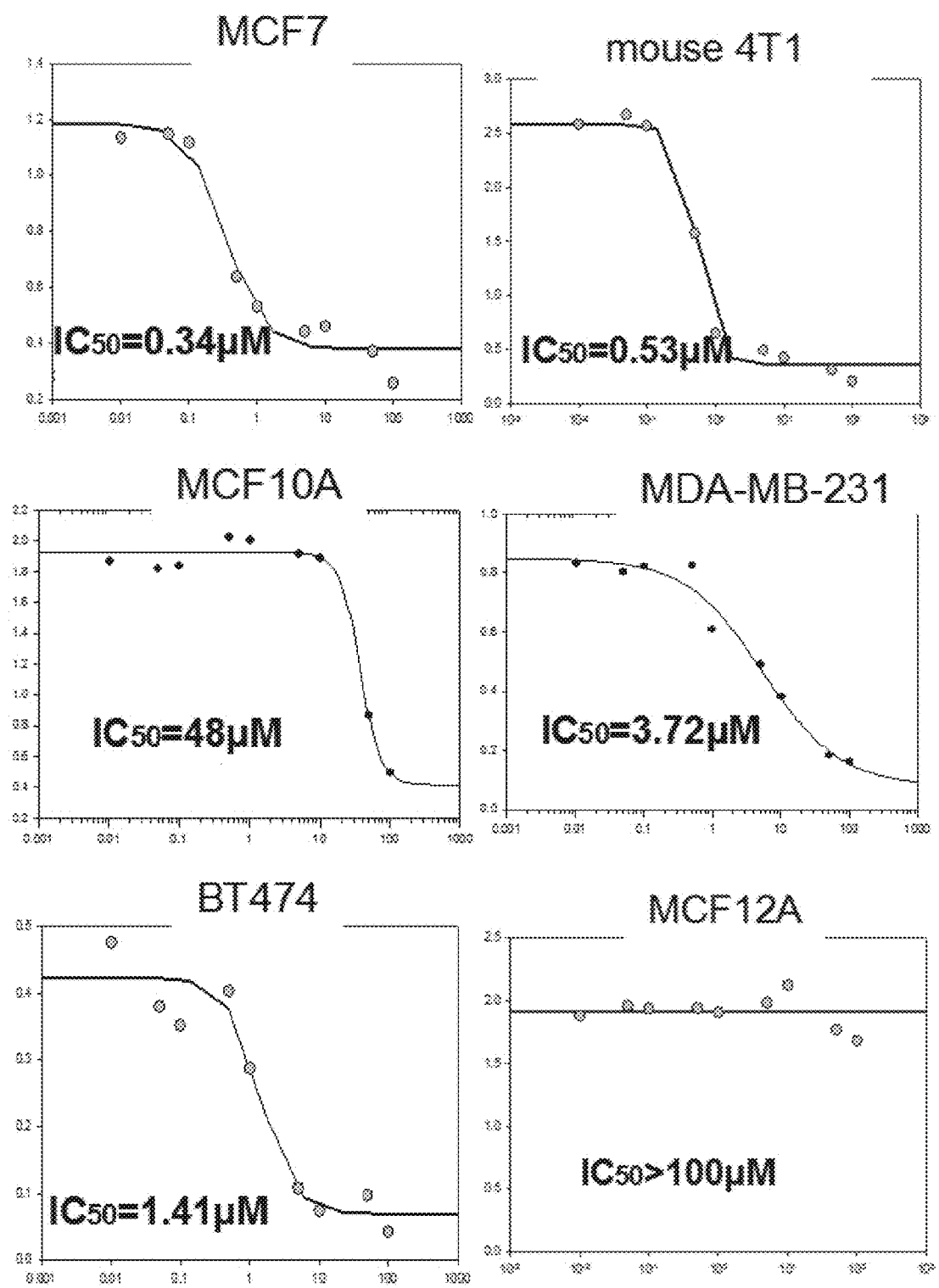
FIG. 1A shows data on the cytotoxicity of HDAB001 in breast carcinoma, ER-positive: MCF7, ER-positive and ERBB2-overexpressing: BT474; ER-negative: MDA-MB-231; mouse mammary carcinoma 4T1; human non-tumor mammary epithelial MCF10A (ER/PR-negative) and MCF12A (ER-positive) cells.

The disclosure relates to Transforming Growth Factor-β-Activated Kinase 1 (TAK1) inhibitors, compositions, and uses related thereto. In certain embodiments, the disclosure relates to compounds of formula I, pharmaceutical compositions having a compound of formula I, and methods of treating or preventing cancer by administering a pharmaceutical composition or pharmaceutically acceptable salt there of having a compound of formula I to a subject in need thereof.

TAK1 Inhibitors

In certain embodiments, the disclosure relates to compounds of formula I,

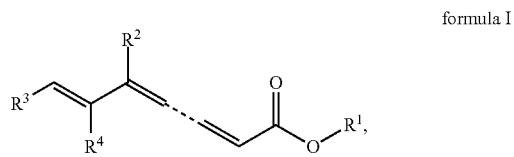

formula I or salts of prodrugs thereof wherein is a single bond with a trans isomer to $R^2$ and a cis isomer to $-(C=O)R^1$, a cis isomer to $R^2$ and a cis isomer to $-(C=O)R^1$; or a trans isomer to $R^2$ and a trans isomer to $-(C=O)R^1$;

$R^1$ is hydrogen, hydroxy, alkyl, alkoxy, carbocyclyl, aryl, or heterocyclyl, wherein $R^1$ is optionally substituted with one or more, the same or different, $R^{10}$;

$R^2$ is formyl, carboxy, carbamoyl, or phosphonate, wherein $R^2$ is optionally substituted with one or more, the same or different, $R^{10}$;

$R^3$ is nitro, cyano, hydroxy, amino, mercapto, formyl, carboxy, carbamoyl, alkylamino, (alkyl)$_2$amino, alkylsulfinyl, alkylsulfonyl, arylsulfonyl, aryl, or heteroaryl wherein $R^3$ is optionally substituted with one or more, the same or different, $R^{10}$;

$R^4$ is hydrogen or $R^3$ and $R^4$ and the attached atoms form an aryl or heteroaryl ring wherein the ring is optionally substituted with one or more, the same or different, $R^{10}$;

$R^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{10}$ is optionally substituted with one or more, the same or different, $R^{11}$;

$R^{11}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{11}$ is optionally substituted with one or more, the same or different, $R^{12}$;

$R^{12}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{12}$ is optionally substituted with one or more, the same or different, $R^{13}$; and $R^{13}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, compounds of formula I have formula IA,

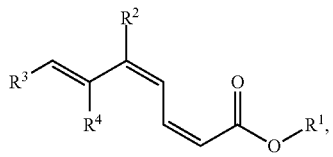

formula IA or salts or prodrugs thereof wherein, $R^1$ is hydrogen, hydroxy, alkyl, alkoxy, carbocyclyl, aryl, or heterocyclyl, wherein $R^1$ is optionally substituted with one or more, the same or different, $R^{10}$;

$R^2$ is formyl, carboxy, carbamoyl, or phosphonate, wherein $R^2$ is optionally substituted with one or more, the same or different, $R^{10}$;

$R^3$ is nitro, cyano, hydroxy, amino, mercapto, formyl, carboxy, carbamoyl, alkylamino, (alkyl)$_2$amino, alkylsulfinyl, alkylsulfonyl, arylsulfonyl, aryl, or heteroaryl wherein $R^3$ is optionally substituted with one or more, the same or different, $R^{10}$;

$R^4$ is hydrogen or $R^3$ and $R^4$ and the attached atoms form an aryl or heteroaryl ring wherein the ring is optionally substituted with one or more, the same or different, $R^{10}$;

$R^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{10}$ is optionally substituted with one or more, the same or different, $R^{11}$;

$R^{11}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{11}$ is optionally substituted with one or more, the same or different, $R^{12}$;

$R^{12}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{12}$ is optionally substituted with one or more, the same or different, $R^{13}$; and $R^{13}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethyl sulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethyl sulfamoyl, carbocyclyl, aryl, or heterocyclyl.

In certain embodiments, compounds of formula I have formula IB, IC or ID,

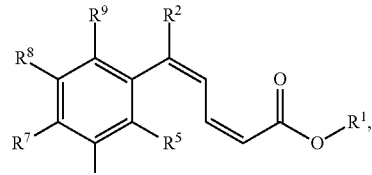

FORMULA IB

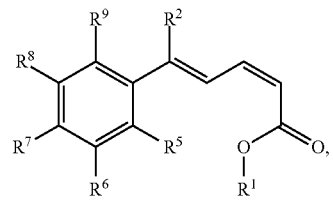

FORMULA IC

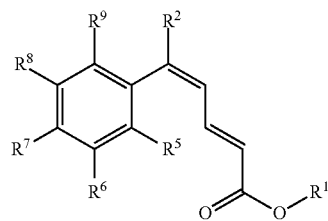

FORMULA ID or salts or prodrugs thereof wherein, $R^1$ is hydrogen, hydroxy, alkyl, alkoxy, carbocyclyl, aryl, or heterocyclyl, wherein $R^1$ is optionally substituted with one or more, the same or different, $R^{10}$;

$R^2$ is formyl, carboxy, or phosphonate, wherein $R^2$ is optionally substituted with one or more, the same or different, $R^{10}$;

$R^5$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^5$ is optionally substituted with one or more, the same or different, $R^{10}$;

$R^6$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^6$ is optionally substituted with one or more, the same or different, $R^{10}$;

$R^7$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^7$ is optionally substituted with one or more, the same or different, $R^{10}$;

$R^8$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^8$ is optionally substituted with one or more, the same or different, $R^{10}$;

$R^9$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^9$ is optionally substituted with one or more, the same or different, $R^{10}$;

$R^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{11}$ is optionally substituted with one or more, the same or different, $R^{11}$;

$R^{11}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{11}$ is optionally substituted with one or more, the same or different, $R^{12}$;

$R^{12}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{12}$ is optionally substituted with one or more, the same or different, $R^{13}$; and $R^{13}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, the disclosure relates to an substituted (2E,4Z)-dialkyl 2-(phenyl)hexa-2,4-dienedioate or derivative.

In certain embodiments, the disclosure relates to a compound selected from (2E,4Z)-dimethyl 2-(3,4-dichlorophenyl)hexa-2,4-dienedioate, (2E,4Z)-dimethyl 2-(4-methoxyphenyl)hexa-2,4-dienedioate, (2E,4Z)-dimethyl 2-(3,4-dimethoxyphenyl)hexa-2,4-dienedioate, (2E,4Z)-dimethyl 2-(3-hydroxyphenyl)hexa-2,4-dienedioate, (2E,4Z)-dimethyl 2-(4-chlorophenyl)hexa-2,4-dienedioate, (2E,4Z)-dimethyl 2-(4-bromophenyl)hexa-2,4-dienedioate, (2E,4Z)-dimethyl 2-(4-iodophenyl)hexa-2,4-dienedioate, (2E,4Z)-dimethyl 2-(4-nitrophenyl)hexa-2,4-dienedioate, (2E,4Z)-dimethyl 2-(4-trifluoromethylphenyl)hexa-2,4-dienedioate, (2E,4Z)-dimethyl 2-(3,5-ditrifluoromethylphenyl)hexa-2,4-dienedioate, (2E,4Z)-dimethyl 2-(4-biphenyl)hexa-2,4-dienedioate, (2E,4Z)-dimethyl 2-(benzofuran-3-yl)hexa-2,4-dienedioate, (1E,3E,5Z)-trimethyl hexa-1,3,5-triene-1,3,6-tricarboxylate, (2E,4E)-dimethyl 4-((Z)-4-oxopent-2-en-1-ylidene)pent-2-enedioate, (2Z,4E)-methyl 5-(4-bromophenyl)-5-(dimethoxyphosphoryl)penta-2,4-dienoate, (2Z,4Z)-dimethyl 2-(3,4-dichlorophenyl)hexa-2,4-dienedioate, (2Z,4Z)-dimethyl 2-(4-bromophenyl)hexa-2,4-dienedioate, (2Z,4Z)-dimethyl 2-(4-iodophenyl)hexa-2,4-dienedioate, (2Z,4Z)-dimethyl 2-(4-nitrophenyl)hexa-2,4-dienedioate, and (2E,4E)-dimethyl 2-(3,4-dichlorophenyl)hexa-2,4-dienedioate.

In certain embodiments, compounds of formula I have formula II,

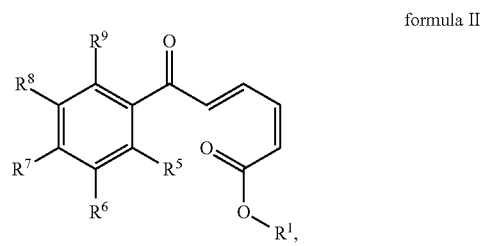

formula II or salts or prodrugs thereof wherein, $R^1$ is hydrogen, hydroxy, alkyl, alkoxy, carbocyclyl, aryl, or heterocyclyl, wherein $R^1$ is optionally substituted with one or more, the same or different, $R^{10}$;

$R^5$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^5$ is optionally substituted with one or more, the same or different, $R^{10}$;

$R^6$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^6$ is optionally substituted with one or more, the same or different, $R^{10}$;

$R^7$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^7$ is optionally substituted with one or more, the same or different, $R^{10}$;

$R^8$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^8$ is optionally substituted with one or more, the same or different, $R^{10}$;

$R^9$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^9$ is optionally substituted with one or more, the same or different, $R^{10}$;

$R^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{10}$ is optionally substituted with one or more, the same or different, $R^{11}$;

$R^{11}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{11}$ is optionally substituted with one or more, the same or different, $R^{12}$;

$R^{12}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{12}$ is optionally substituted with one or more, the same or different, $R^{13}$; and $R^{13}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethyl sulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

Method for Preparing Inhibitors

Compounds disclosed herein may be prepared using methods provided for in the examples and as provided for, or as appropriately modified by a skilled artisan, in Hahn et al., Journal of Organometallic Chemistry, (2004), 689(16), 2662-2673 and Hedley et al., J. Org. Chem., 2006, 71 (14), 5349-5356.

In certain embodiments, the disclosure relates to methods of isolating compounds disclosed herein prepared using the procedures outlined below.

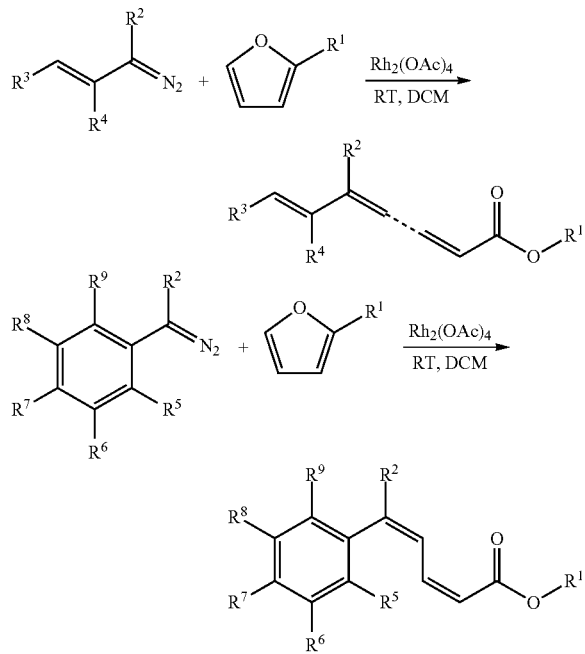

Uses of TAK1 Inhibitors

In certain embodiments, the disclosure relates to uses of compounds disclosed herein in the production of a medicament for the treatment of a cancer.

In certain embodiments, the subject is at a greater risk of metastases, e.g., diagnosed with metastases or because the subject is experiencing a recurrence of cancer. Subjects with advanced breast cancers (BCs) frequently develop skeletal metastases that cause pain, bone fractures and other complications. Current therapies for bone metastases (antiestrogens, bisphosphonates, etc) have limited effect in prolonging the lifespan or bone loss in patients. TAK1 has a role in breast cancer skeletal metastases. See Safina et al., TAK1-TAB2 Signaling Contributes to Bone Destruction by Breast Carcinoma Cells, Molecular Cancer Research, 2011, 9, 1042-1053. Safina et al. report that tumor cells injected into the left cardiac ventricle induce osteoclast-mediated bone destruction, and inhibition of TAK1 with a dominant-negative TAK1-K63W mutant in MDA-MB-231 blocked formation of osteolytic bone lesions, whereas 80% of mice in the control group had lesions. DnTAK1 reduced amount of TRAP-positive cells at the tumor-bone interface. TAK1 regulates genes involved in invasion (MMP9, COX2) and "the vicious cycle" (PTHrP, IL8). TAK1 does not affect IL11 and CTGF that are known to be controlled via the TGF-β-Smad and TGF-β-Src signaling. Thus, inhibition of TAK1 signaling with compound disclosed herein provides a method to reduce tumor bone metastases.

In certain embodiments, the disclosure relates to methods of treating or preventing cancer comprising administering a pharmaceutical composition comprising compounds disclosed herein to a subject at risk of, exhibiting symptoms of, or diagnosed with cancer. In certain embodiments, the subject is diagnosed with a tumor or malignant tumors derived from epithelial cells such as breast, prostate, lung and colon cancer.

Examples of cancers or proliferative disorders which can be the primary tumor that is treated include but are not limited to neoplasms located in the: colon, abdomen, bone, breast, digestive system, liver, pancreas, peritoneum, endocrine glands (adrenal, parathyroid, pituitary, testicles, ovary, thymus, thyroid), eye, head and neck, nervous (central and peripheral), lymphatic system, pelvis, skin, soft tissue, spleen, thorax, prostate, and urogenital tract.

In certain embodiments, the subject is diagnosed with acute childhood lymphoblastic leukemia; acute lymphoblastic leukemia, acute lymphocytic leukemia, acute myeloid leukemia, adrenocortical carcinoma, adult (primary) hepatocellular cancer, adult (primary) liver cancer, adult acute lymphocytic leukemia, adult acute myeloid leukemia, adult Hodgkin's disease, adult Hodgkin's lymphoma, adult lymphocytic leukemia, adult non-Hodgkin's lymphoma, adult primary liver cancer, adult soft tissue sarcoma, AIDS-related lymphoma, AIDS-related malignancies, anal cancer, astrocytoma, bile duct cancer, bladder cancer, bone cancer, brain stem glioma, brain tumors, breast cancer, cancer of the renal pelvis and ureter, central nervous system (primary) lymphoma, central nervous system lymphoma, cerebellar astrocytoma, cerebral astrocytoma, cervical cancer, childhood (primary) hepatocellular cancer, childhood (primary) liver cancer, childhood acute lymphoblastic leukemia, childhood acute myeloid leukemia, childhood brain stem glioma, childhood cerebellar astrocytoma, childhood cerebral astrocytoma, childhood extracranial germ cell tumors, childhood Hodgkin's disease, childhood Hodgkin's lymphoma, childhood hypothalanic and visual pathway glioma, childhood lymphoblastic leukemia, childhood medulloblastoma, childhood non-Hodgkin's lymphoma, childhood pineal and supratentorial primitive neuroectodermal tumors, childhood primary liver cancer, childhood rhabdomyosarcoma, childhood soft tissue sarcoma, childhood visual pathway and hypothalamic glioma, chronic lymphocytic leukemia, chronic myelogenous leukemia, colon cancer, cutaneous T-cell lymphoma, endocrine pancreas Islet cell carcinoma, endometrial cancer, ependymoma, epithelial cancer, esophageal cancer, Ewing's sarcoma and related tumors, exocrine pancreatic cancer, extracranial germ cell tumor, extragonadal germ cell tumor, extrahepatie bile duct cancer, eye cancer, female Breast cancer, Gaucher's disease, gallbladder cancer, gastric cancer, gastrointestinal carcinoid tumor, gastrointestinal tumors, germ cell tumors, gestational trophoblastic tumor, hairy cell leukemia, head and neck cancer, hepatocellular cancer, Hodgkin's disease, Hodgkin's lymphoma, hypergammaglobulinemia, hypopharyngeal cancer, intestinal cancers, intraocular melanoma, islet cell carcinoma, islet cell pancreatic cancer, Kaposi's sarcoma, kidney cancer, laryngeal cancer, lip and oral cavity cancer, liver cancer, lung cancer, lympho proliferative disorders, macroglobulinemia, male breast cancer, malignant mesothelioma, malignant thymoma, medulloblastomia, melanoma, mesothelioma, metastatie occult primary squamous neck cancer, metastatie primary squamous neck cancer, metastatie squamous neck cancer, multiple myeloma, multiple myeloma/plasma cell neoplasm, myelodysplasia syndrome, myelogenous leukemia, myeloid leukemia, myeloproliferative disorders, nasal cavity and paranasal sinus cancer, nasopharyngeal cancer, neuroblastoma, non-Hodgkin's lymphoma during pregnancy, nonmelanoma skin cancer, non-small cell lung cancer, occult primary metastatie squamous neck cancer, oropharyngeal cancer, osteo/malignant fibrous sarcoma, osteosarcoma/malignant fibrous histiocytoma, osteosarcoma/malignant fibrous histiocytoma of bone, ovarian epithelial cancer, ovarian germ cell tumor, ovarian low malignant potential tumor, pancreatic cancer, paraproteinemias, purpura, parathyroid, cancer, penile cancer, pheochromocytoma, pituitary tumor, plasma cell neoplasm/multiple myeloma, primary central nervous system lymphoma, primary liver cancer, prostate cancer, rectal cancer, renal cell cancer, renal pelvis and ureter cancer, retinoblastoma, rhabdomyosarcoma, salivary gland cancer, sarcoidosis sarcomas, sezary syndrome, skin cancer, small cell lung cancer, small Intestine cancer, soft tissue sarcoma, squamous neck cancer, stomach cancer, supratentorial primitive neuroectodermal and pineal tumors, T-ceII lymphoma, testicular cancer, thymoma, thyroid cancer, transitional cell cancer of the renal pelvis and ureter, transitional renal pelvis and ureter cancer, trophoblastic tumors, ureter and renal pelvis cell cancer, urethial cancer, uterine cancer, uterine sarcoma, vaginal cancer, visual pathway and Hypothalamic glioma, vulvar cancer, Waldenstrom's macroglobulinemia, Wilm's tumor, and any other hyperproliferative disease located in an organ system listed above.

In certain embodiments, the cancer symptoms may be local symptoms such as unusual lumps or swelling (tumor), hemorrhage (bleeding), pain and/or ulceration or symptoms of metastasis (spreading) such as enlarged lymph nodes, cough and hemoptysis, hepatomegaly (enlarged liver), bone pain, fracture of affected bones and neurological symptoms or systemic symptoms such as weight loss, poor appetite, fatigue and cachexia (wasting), excessive sweating (night sweats), anemia and specific paraneoplastic phenomena, i.e. specific conditions that are due to an active cancer, such as thrombosis or hormonal changes.

In certain embodiments, a subject may be at risk of cancer because of genetics, tobacco use, obesity, viral infections, radiation exposure, stress, lack of physical activity, and environmental pollutants.
Combination Therapies The anti-cancer treatment defined herein may be applied as a sole therapy or may involve, conventional surgery or radiotherapy or chemotherapy. Such chemotherapy may include one or more of the following categories of antitumour agents:

(i) antiproliferative/antineoplastic drugs and combinations thereof, as used in medical oncology, such as alkylating agents (for example cis-platin, carboplatin, cyclophosphamide, nitrogen mustard, melphalan, chlorambucil, busulfan and nitrosoureas); antimetabolites (for example antifolates such as fluoropyrimidines like 5-fluorouracil and gemcitabine, tegafur, raltitrexed, methotrexate, cytosine arabinoside and hydroxyurea); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere); and topoisomerase inhibitors (for example epipodophyllotoxins like etoposide and teniposide, amsacrine, topotecan and camptothecin); and proteosome inhibitors (for example bortezomib [Velcade®]); and the agent anegrilide [Agrylin®]; and the agent alpha-interferon (ii) cytostatic agents such as antioestrogens (for example tamoxifen, toremifene, raloxifene, droloxifene and iodoxyfene), oestrogen receptor down regulators (for example fulvestrant), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) agents which inhibit cancer cell invasion (for example metalloproteinase inhibitors like marimastat and inhibitors of urokinase plasminogen activator receptor function);

(iv) inhibitors of growth factor function, for example such inhibitors include growth factor antibodies, growth factor receptor antibodies (for example the anti-Her2 antibody trastuzumab and the anti-epidermal growth factor receptor (EGFR) antibody, cetuximab), farnesyl transferase inhibitors, tyrosine kinase inhibitors and serine/threonine kinase inhibitors, for example inhibitors of the epidermal growth factor family (for example EGFR family tyrosine kinase inhibitors such as: N-(3-chloro-4-fluorophenyl)-7-methoxy-6-(3-morpholinopropoxy)quinazolin-4-amine (gefitinib), N-(3-ethynylphenyl)-6,7-bis(2-methoxyethoxy)quinazolin-4-amine (erlotinib), and 6-acrylamido-N-(3-chloro-4-fluorophenyl)-7-(3-morpholinopropoxy)quinazolin-4-amine (CI 1033), for example inhibitors of the platelet-derived growth factor family and for example inhibitors of the hepatocyte growth factor family, for example inhibitors or phosphotidylinositol 3-kinase (PI3K) and for example inhibitors of mitogen activated protein kinase kinase (MEK1/2) and for example inhibitors of protein kinase B (PKB/Akt), for example inhibitors of Src tyrosine kinase family and/or Abelson (AbI) tyrosine kinase family such as dasatinib (BMS-354825) and imatinib mesylate (Gleevec™); and any agents that modify STAT signalling;

(v) antiangiogenic agents such as those which inhibit the effects of vascular endothelial growth factor, (for example the anti-vascular endothelial cell growth factor antibody bevacizumab [Avastin™]) and compounds that work by other mechanisms (for example linomide, inhibitors of integrin ocvβ3 function and angiostatin);

(vi) vascular damaging agents such as Combretastatin A4;

(vii) antisense therapies, for example those which are directed to the targets listed above, such as an anti-ras antisense; and (viii) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies, and approaches using the immunomodulatory drugs thalidomide and lenalidomide [Revlimid®].

Pharmaceutical Formulations

Pharmaceutical compositions disclosed herein may be in the form of pharmaceutically acceptable salts, as generally described below. Some preferred, but non-limiting examples of suitable pharmaceutically acceptable organic and/or inorganic acids are hydrochloric acid, hydrobromic acid, sulfuric acid, nitric acid, acetic acid and citric acid, as well as other pharmaceutically acceptable acids known per se (for which reference is made to the references referred to below).

When the compounds of the disclosure contain an acidic group as well as a basic group, the compounds of the disclosure may also form internal salts, and such compounds are within the scope of the disclosure. When the compounds contain a hydrogen-donating heteroatom (e.g. NH), this disclosure contemplates salts and/or isomers formed by transfer of said hydrogen atom to a basic group or atom within the molecule, such as in the case of an amino acid.

Pharmaceutically acceptable salts of the compounds include the acid addition and base salts thereof. Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, i sethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts. Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulphate and hemicalcium salts. For a review on suitable salts, see Handbook of Pharmaceutical Salts: Properties, Selection, and Use by Stahl and Wermuth (Wiley-VCH, 2002), incorporated herein by reference.

The compounds described herein may be administered in the form of prodrugs. A prodrug can include a covalently bonded carrier which releases the active parent drug when administered to a mammalian subject. Prodrugs can be prepared by modifying functional groups present in the compounds in such a way that the modifications are cleaved, either in routine manipulation or in vivo, to the parent compounds. Prodrugs include, for example, compounds wherein a hydroxyl group is bonded to any group that, when administered to a mammalian subject, cleaves to form a free hydroxyl group. Examples of prodrugs include, but are not limited to, acetate, formate and benzoate derivatives of alcohol functional groups in the compounds. Methods of structuring a compound as prodrugs can be found in the book of Testa and Mayer, Hydrolysis in Drug and Prodrug Metabolism, Wiley (2006). Typical prodrugs form the active metabolite by transformation of the prodrug by hydrolytic enzymes, the hydrolysis of amide, lactams, peptides, carboxylic acid esters, epoxides or the cleavage of esters of inorganic acids.

Pharmaceutical compositions for use in the present disclosure typically comprise an effective amount of a compound and a suitable pharmaceutical acceptable carrier. The preparations may be prepared in a manner known per se, which usually involves mixing the at least one compound according to the disclosure with the one or more pharmaceutically acceptable carriers, and, if desired, in combination with other pharmaceutical active compounds, when necessary under aseptic conditions. Reference is again made to U.S. Pat. Nos. 6,372,778, 6,369,086, 6,369,087, and 6,372,733 and the further references mentioned above, as well as to the standard handbooks, such as the latest edition of Remington's Pharmaceutical Sciences.

Generally, for pharmaceutical use, the compounds may be formulated as a pharmaceutical preparation comprising at least one compound and at least one pharmaceutically acceptable carrier, diluent or excipient and/or adjuvant, and optionally one or more further pharmaceutically active compounds.

The pharmaceutical preparations of the disclosure are preferably in a unit dosage form, and may be suitably packaged, for example in a box, blister, vial, bottle, sachet, ampoule or in any other suitable single-dose or multi-dose holder or container (which may be properly labeled); optionally with one or more leaflets containing product information and/or instructions for use. Generally, such unit dosages will contain between 1 and 1000 mg, and usually between 5 and 500 mg, of the at least one compound of the disclosure, e.g. about 10, 25, 50, 100, 200, 300 or 400 mg per unit dosage.

The compounds can be administered by a variety of routes including the oral, ocular, rectal, transdermal, subcutaneous, intravenous, intramuscular or intranasal routes, depending mainly on the specific preparation used. The compound will generally be administered in an "effective amount", by which is meant any amount of a compound that, upon suitable administration, is sufficient to achieve the desired therapeutic or prophylactic effect in the subject to which it is administered. Usually, depending on the condition to be prevented or treated and the route of administration, such an effective amount will usually be between 0.01 to 1000 mg per kilogram body weight of the patient per day, more often between 0.1 and 500 mg, such as between 1 and 250 mg, for example about 5, 10, 20, 50, 100, 150, 200 or 250 mg, per kilogram body weight of the patient per day, which may be administered as a single daily dose, divided over one or more daily doses. The amount(s) to be administered, the route of administration and the further treatment regimen may be determined by the treating clinician, depending on factors such as the age, gender and general condition of the patient and the nature and severity of the disease/symptoms to be treated. Reference is made to U.S. Pat. Nos. 6,372,778, 6,369,086, 6,369,087, and 6,372,733 and the further references mentioned above, as well as to the standard handbooks, such as the latest edition of Remington's Pharmaceutical Sciences.

For an oral administration form, the compound can be mixed with suitable additives, such as excipients, stabilizers or inert diluents, and brought by means of the customary methods into the suitable administration forms, such as tablets, coated tablets, hard capsules, aqueous, alcoholic, or oily solutions. Examples of suitable inert carriers are gum arabic, magnesia, magnesium carbonate, potassium phosphate, lactose, glucose, or starch, in particular, corn starch. In this case, the preparation can be carried out both as dry and as moist granules. Suitable oily excipients or solvents are vegetable or animal oils, such as sunflower oil or cod liver oil. Suitable solvents for aqueous or alcoholic solutions are water, ethanol, sugar solutions, or mixtures thereof. Polyethylene glycols and polypropylene glycols are also useful as further auxiliaries for other administration forms. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, the compositions may be prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. Suitable pharmaceutical formulations for administration in the form of aerosols or sprays are, for example, solutions, suspensions or emulsions of the compounds of the disclosure or their physiologically tolerable salts in a pharmaceutically acceptable solvent, such as ethanol or water, or a mixture of such solvents. If required, the formulation can also additionally contain other pharmaceutical auxiliaries such as surfactants, emulsifiers and stabilizers as well as a propellant.

For subcutaneous or intravenous administration, the compounds, if desired with the substances customary therefore such as solubilizers, emulsifiers or further auxiliaries are brought into solution, suspension, or emulsion. The compounds of formula I can also be lyophilized and the lyophilizates obtained used, for example, for the production of injection or infusion preparations. Suitable solvents are, for example, water, physiological saline solution or alcohols, e.g. ethanol, propanol, glycerol, sugar solutions such as glucose or mannitol solutions, or mixtures of the various solvents mentioned. The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, the formulations may be prepared by mixing the compounds of formula I with a suitable non-irritating excipient, such as cocoa butter, synthetic glyceride esters or polyethylene glycols, which are solid at ordinary temperatures, but liquefy and/or dissolve in the rectal cavity to release the drug.

In certain embodiments, it is contemplated that these compositions can be extended release formulations. Typical extended release formations utilize an enteric coating. A barrier is applied to oral medication that controls the location in the digestive system where it is absorbed. Enteric coatings prevent release of medication before it reaches the small intestine. Enteric coatings may contain polymers of polysaccharides, such as maltodextrin, xanthan, scleroglucan dextran, starch, alginates, pullulan, hyaluronic acid, chitin, chitosan and the like; other natural polymers, such as proteins (albumin, gelatin etc.), poly-L-lysine; sodium poly (acrylic acid); poly(hydroxyalkylmethacrylates) (for example poly(hydroxyethylmethacrylate)); carboxypolymethylene (for example Carbopol™); carbomer; polyvinylpyrrolidone; gums, such as guar gum, gum arabic, gum karaya, gum ghatti, locust bean gum, tamarind gum, gellan gum, gum tragacanth, agar, pectin, gluten and the like; poly(vinyl alcohol); ethylene vinyl alcohol; polyethylene glycol (PEG); and cellulose ethers, such as hydroxymethylcellulose (HMC), hydroxyethylcellulose (HEC), hydroxypropylcellulose (HPC), methylcellulose (MC), ethylcellulose (EC), carboxyethylcellulose (CEC), ethylhydroxyethylcellulose (EHEC), carboxymethylhydroxyethylcellulo se (CMHEC), hydroxypropylmethyl-cellulose (HPMC), hydroxypropylethylcellulose (HPEC) and sodium carboxymethylcellulose (Na CMC); as well as copolymers and/or (simple) mixtures of any of the above polymers. Certain of the above-mentioned polymers may further be crosslinked by way of standard techniques.

The choice of polymer will be determined by the nature of the active ingredient/drug that is employed in the composition of the disclosure as well as the desired rate of release. In particular, it will be appreciated by the skilled person, for example in the case of HPMC, that a higher molecular weight will, in general, provide a slower rate of release of drug from the composition.

Furthermore, in the case of HPMC, different degrees of substitution of methoxyl groups and hydroxypropoxyl groups will give rise to changes in the rate of release of drug from the composition. In this respect, and as stated above, it may be desirable to provide compositions of the disclosure in the form of coatings in which the polymer carrier is provided by way of a blend of two or more polymers of, for example, different molecular weights in order to produce a particular required or desired release profile.

Terms

A "metal catalyst" refers to a metal complex optionally with organic ligands. Examples include $Rh_2(OAc)_4$, $Rh_2(S\text{-biTISP})_2$, $Rh_2(S\text{-DOSP})_4$, or $Rh_2(S\text{-PTAD})_4$ catalysts as disclosed in Denton & Davis, Organic Letters, 2009, 11(4), 787-790, Davis et al., Tetrahedron Letters, 1996, 37(24) 4133-4136, and U.S. Pat. No. 7,385,064 hereby incorporated by reference.

As used herein, "alkyl" means a noncyclic straight chain or branched, unsaturated or saturated hydrocarbon such as those containing from 1 to 10 carbon atoms, while the term "lower alkyl" or "$C_{1-4}$alkyl" has the same meaning as alkyl but contains from 1 to 4 carbon atoms. The term "higher alkyl" has the same meaning as alkyl but contains from 7 to 20 carbon atoms.

Representative saturated straight chain alkyls include methyl, ethyl, n-propyl, n-butyl, n-pentyl, n-hexyl, n-septyl, n-octyl, n-nonyl, and the like; while saturated branched alkyls include isopropyl, sec-butyl, isobutyl, tert-butyl, isopentyl, and the like. Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

Non-aromatic mono or polycyclic alkyls are referred to herein as "carbocycles" or "carbocyclyl" groups. Representative saturated carbocycles include cyclopropyl, cyclobutyl, cyclopentyl, cyclohexyl, and the like; while unsaturated carbocycles include cyclopentenyl and cyclohexenyl, and the like.

"Heterocarbocycles" or heterocarbocyclyl" groups are carbocycles which contain from 1 to 4 heteroatoms independently selected from nitrogen, oxygen and sulfur which may be saturated or unsaturated (but not aromatic), monocyclic or polycyclic, and wherein the nitrogen and sulfur heteroatoms may be optionally oxidized, and the nitrogen heteroatom may be optionally quaternized. Heterocarbocycles include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

"Aryl" means an aromatic carbocyclic monocyclic or polycyclic ring such as phenyl or naphthyl. Polycyclic ring systems may, but are not required to, contain one or more non-aromatic rings, as long as one of the rings is aromatic.

As used herein, "heteroaryl" refers an aromatic heterocarbocycle having 1 to 4 heteroatoms selected from nitrogen, oxygen and sulfur, and containing at least 1 carbon atom, including both mono- and polycyclic ring systems. Polycyclic ring systems may, but are not required to, contain one or more non-aromatic rings, as long as one of the rings is aromatic. Representative heteroaryls are furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl. It is contemplated that the use of the term "heteroaryl" includes N-alkylated derivatives such as a 1-methylimidazol-5-yl substituent.

As used herein, "heterocycle" or "heterocyclyl" refers to mono- and polycyclic ring systems having 1 to 4 heteroatoms selected from nitrogen, oxygen and sulfur, and containing at least 1 carbon atom. The mono- and polycyclic ring systems may be aromatic, non-aromatic or mixtures of aromatic and non-aromatic rings. Heterocycle includes heterocarbocycles, heteroaryls, and the like.

"Alkylthio" refers to an alkyl group as defined above with the indicated number of carbon atoms attached through a sulfur bridge. An example of an alkylthio is methylthio, (i.e., —S—CH3).

"Alkoxy" refers to an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. Preferred alkoxy groups are methoxy, ethoxy, n-propoxy, propoxy, n-butoxy, s-butoxy, t-butoxy.

"Alkylamino" refers an alkyl group as defined above with the indicated number of carbon atoms attached through an amino bridge. An example of an alkylamino is methylamino, (i.e., —NH—CH3).

"Alkanoyl" refers to an alkyl as defined above with the indicated number of carbon atoms attached through a carbonyl bride (i.e., —(C═O)alkyl).

"Alkylsulfonyl" refers to an alkyl as defined above with the indicated number of carbon atoms attached through a sulfonyl bridge (i.e., —S(═O)2alkyl) such as mesyl and the like, and "Arylsulfonyl" refers to an aryl attached through a sulfonyl bridge (i.e., —S(═O)2aryl).

"Alkylsulfamoyl" refers to an alkyl as defined above with the indicated number of carbon atoms attached through a sulfamoyl bridge (i.e., —NHS(═O)2alkyl), and an "Arylsulfamoyl" refers to an alkyl attached through a sulfamoyl bridge (i.e., (i.e., —NHS(═O)2aryl).

"Alkylsulfinyl" refers to an alkyl as defined above with the indicated number of carbon atoms attached through a sulfinyl bridge (i.e. —S(═O)alkyl).

The term "substituted" refers to a molecule wherein at least one hydrogen atom is replaced with a substituent. When substituted, one or more of the groups are "substituents." The molecule may be multiply substituted. In the case of an oxo substituent ("═O"), two hydrogen atoms are replaced. Example substituents within this context may include halogen, hydroxy, alkyl, alkoxy, nitro, cyano, oxo, carbocyclyl, carbocycloalkyl, heterocarbocyclyl, heterocarbocycloalkyl, aryl, arylalkyl, heteroaryl, heteroarylalkyl, —NRaRb, —NRaC(═O)Rb, —NRaC(═O)NRaNRb, —NRaC(═O)ORb, —NRaSO2Rb, —C(═O)Ra, —C(═O)ORa, —C(═O)NRaRb, —OC(═O)NRaRb, —ORa, —SRa, —SORa, —S(═O)2Ra, —OS(═O)2Ra and —S(═O)2ORa. Ra and Rb in this context may be the same or different and independently hydrogen, halogen, hydroxyl, alkyl, alkoxy, alkyl, amino, alkylamino, dialkylamino, carbocyclyl, carb ocycloalkyl, heterocarb ocyclyl, heterocarbocycloalkyl, aryl, arylalkyl, heteroaryl, heteroarylalkyl.

The term "optionally substituted," as used herein, means that substitution is optional and therefore it is possible for the designated atom to be unsubstituted.

As used herein, the term "derivative" refers to a structurally similar compound that retains sufficient functional attributes of the identified analogue. The derivative may be structurally similar because it is lacking one or more atoms, substituted, a salt, in different hydration/oxidation states, or because one or more atoms within the molecule are switched, such as, but not limited to, replacing a oxygen atom with a sulfur atom or replacing a amino group with a hydroxyl group. The derivative may be a prodrug. Derivatives can be prepare by any variety of synthetic methods or appropriate adaptations presented in synthetic or organic chemistry text books, such as those provide in March's Advanced Organic Chemistry: Reactions, Mechanisms, and Structure, Wiley, 6th Edition (2007) Michael B. Smith or Domino Reactions in Organic Synthesis, Wiley (2006) Lutz F. Tietze.

As used herein, "salts" refer to derivatives of the disclosed compounds where the parent compound is modified making acid or base salts thereof. Examples of salts include, but are not limited to, mineral or organic acid salts of basic residues such as amines, alkylamines, or dialkylamines; alkali or organic salts of acidic residues such as carboxylic acids; and the like. In preferred embodiment the salts are conventional nontoxic pharmaceutically acceptable salts including the quaternary ammonium salts of the parent compound formed, and non-toxic inorganic or organic acids. Preferred salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

"Subject" refers any animal, preferably a human patient, livestock, or domestic pet.

The term "prodrug" refers to an agent that is converted into a biologically active form in vivo. Prodrugs are often useful because, in some situations, they may be easier to administer than the parent compound. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis.

As used herein, the terms "prevent" and "preventing" include the prevention of the recurrence, spread or onset. It is not intended that the present disclosure be limited to complete prevention. In some embodiments, the onset is delayed, or the severity of the disease is reduced.

As used herein, the terms "treat" and "treating" are not limited to the case where the subject (e.g. patient) is cured and the disease is eradicated. Rather, embodiments, of the present disclosure also contemplate treatment that merely reduces symptoms, and/or delays disease progression.

"Cancer" refers any of various cellular diseases with malignant neoplasms characterized by the proliferation of cells. It is not intended that the diseased cells must actually invade surrounding tissue and metastasize to new body sites. Cancer can involve any tissue of the body and have many different forms in each body area. Within the context of certain embodiments, whether "cancer is reduced" may be identified by a variety of diagnostic manners known to one skill in the art including, but not limited to, observation the reduction in size or number of tumor masses or if an increase of apoptosis of cancer cells observed, e.g., if more than a 5% increase in apoptosis of cancer cells is observed for a sample compound compared to a control without the compound. It may also be identified by a change in relevant biomarker or gene expression profile, such as PSA for prostate cancer, HER2 for breast cancer, or others.

EXPERIMENTAL

Synthesis of Aryl Diazoacetates: Representative Procedure

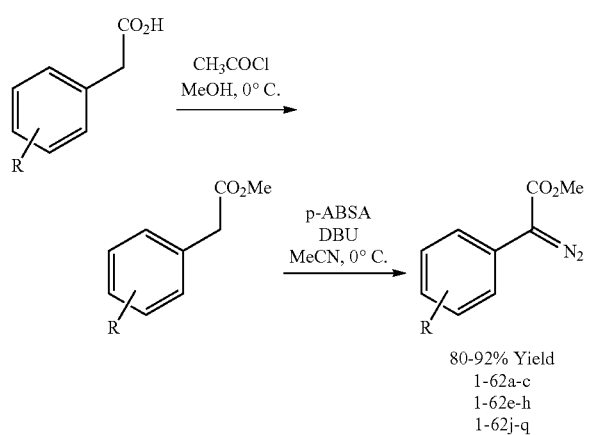

In a flame dried round bottom flask, 2-(4-bromophenyl) acetic acid (50 mmol, 1 eq.) was dissolved in MeOH (50 mL) and cooled to 0° C. Acetyl chloride (60 mmol, 1.2 eq.) was added drop wise at 0° C. The resultant reaction mixture was stirred at rt for overnight. The reaction mixture was poured in to a separation funnel having ethyl ether and saturated NH$_4$Cl. Extracted twice; combined organic layers were washed with brine, dried over magnesium sulfate and concentrated in vacuo. The crude methyl acetate mixture was taken to next step without further purification.

The resultant methyl acetate was dissolved in acetonitrile and p-acetamidobenzene sulfonyl azide (p-ABSA) (60 mmol, 1.2 eq.) was added. The reaction mixture was cooled to 0° C. and 1,8-Diazabicycloundec-7-ene (DBU) (120 mmol, 2 eq.) was added drop wise at 0° C. The reaction mixture was stirred at rt for overnight. Reaction mixture was quenched with saturated aqueous NH4Cl solution, extracted twice with diethyl ether (2×100 mL); combined organic layers were washed with brine, dried over anhydrous MgSO$_4$ and concentrated in vacuo. The residue was purified by flash chromatography on silica gel using 9:1 hexane/Et$_2$O as eluant to isolate 11.16 g (93% yield) of yellow crystalline solid.

Methyl 2-diazo-2-(3,4-dichlorophenyl) acetate (1-62a)

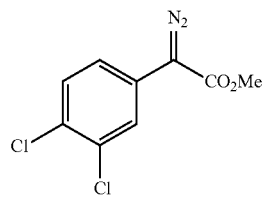

$^1$H NMR (500 MHz, CDCl$_3$): δ7.64 (s, 1H), 7.43 (d, 1H, J=8.5 Hz), 7.28 (d, 1H, J=8.5 Hz), 3.87 (s, 3H). (94% Yield). See Kester & Sarabu WO/2002/008209.

Methyl 2-diazo-2-(4-methoxyphenyl) acetate (1-62b)

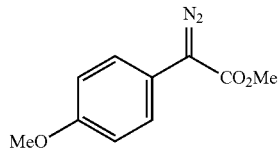

$^1$H NMR (500 MHz, CDCl$_3$): δ7.39 (d, 2H, J=8.5 Hz), 6.94 (d, 2H, J=8.5 Hz), 3.85 (s, 3H), 3.81 (s, 3H). (82% Yield).

Methyl 2-diazo-2-(3,4-dimethoxyphenyl) acetate (1-62c)

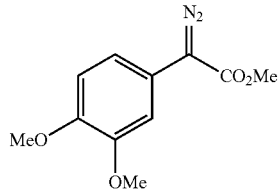

¹H NMR (500 MHz, CDCl₃): δ7.13 (s, 1H), 7.03 (d, 2H, J=8.5 Hz), 3.90 (s, 3H), 3.88 (s, 3H), 3.86 (s, 3H). (93% Yield). See Peschko & Steglich. Tetrahedron Lett., 2000, 41, 9477-9481.

Methyl 2-(benzofuran-3-yl)-2-diazoacetate (1-62d)

¹H NMR (500 MHz, CDCl₃): δ 8.07 (d, 1H, J=8 Hz), 7.65 (t, 1H, J=8 Hz), 7.55 (d, 1H, J=7.5 Hz), 7.47 (t, 1H, J=8 Hz), 3.82 (s, 3H). See Davies & Townsend, Org. Chem., 2001, 66, 6595-6603

Methyl 2-(benzo[d]oxazol-2-yl)-2-diazoacetate (1-62h)

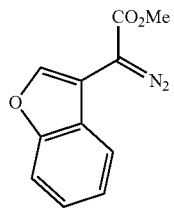

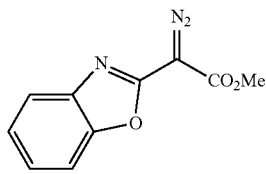

¹H NMR (500 MHz, CDCl₃): δ 7.52 (dd, 2H, J=8 Hz), 7.35 (t, 1H, J=7.5 Hz), 7.26 (t, 1H, J=8 Hz), 3.90 (s, 3H). See Werkhoven et al., J. Eur. J. Org. Chem. 1999, 2909-2914.

Methyl 2-(3-(tert-butyldimethylsilyloxy) phenyl)-2-diazoacetate (1-62e)

¹H NMR (500 MHz, CDCl₃): δ 7.67 (d, 1H, J=7 Hz), 7.53 (d, 1H, J=7.5 Hz), 7.32-7.27 (m, 2H), 3.96 (s, 3H). See Davies & Townsend, Org. Chem., 2001, 66, 6595-6603

Methyl 2-(4-chlorophenyl)-2-diazoacetate (1-62j)

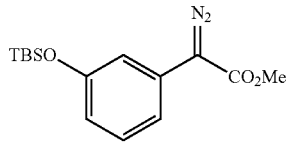

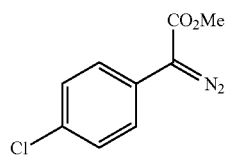

¹H NMR (500 MHz, CDCl₃): δ 7.28 (t, 1H, J=8 Hz), 6.90-6.83 (m, 3H), 3.83 (s, 3H), 0.90 (s, 9H) 0.09 (s, 6H). See Meanwell et al. Drug Des. Discovery 1994, 11, 73-89.

Methyl 2-(1-diazo-2-methoxy-2-oxoethyl) benzoate (1-62f)

¹H NMR (500 MHz, CDCl₃): δ7.42 (d, 2H, J=8.5 Hz), 7.34(d, 2H, J=8.5 Hz), 3.86 (s, 3H). See Ibata et al., Bull. Chem. Soc. Jpn., 1984, 57, 2450-5.

Methyl 2-(4-bromophenyl)-2-diazoacetate (1-62k)

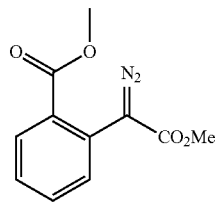

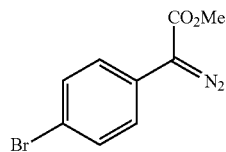

¹H NMR (500 MHz, CDCl₃): δ 8.02 (d, 1H, J=8 Hz), 7.58 (t, 1H, J=8 Hz), 7.53 (d, 1H, J=7.5 Hz), 7.41 (t, 1H, J=8 Hz), 3.92 (s, 3H), 3.84 (s, 3H). See Hamaguchi & Ibata, Chem. Lett., 1976, 287-8.

Methyl 2-diazo-2-(2-nitrophenyl)acetate (1-62g)

¹H NMR (500 MHz, CDCl₃): δ7.50 (d, 2H, J=8.5 Hz), 7.36(d, 2H, J=8.5 Hz), 3.86 (s, 3H). See Baum et al., Synth. Commun., 1987, 17, 1709-16.

Methyl 2-diazo-2-(4-iodophenyl) acetate (1-62l)

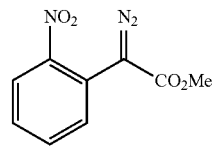

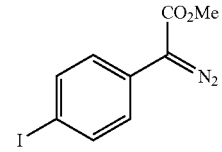

¹H NMR (500 MHz, CDCl₃): δ7.68 (d, 2H, J=8.5 Hz), 7.23(d, 2H, J=8.5 Hz), 3.86 (s, 3H). See Baum et al., Synth. Commun., 1987, 17, 1709-16 and Ni et al., *J. Org. Chem.* 2006, 71, 5594-5598.

Methyl 2-diazo-2-(4-nitrophenyl) acetate (1-62m)

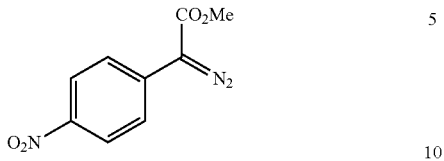

¹H NMR (500 MHz, CDCl₃): δ8.22 (t, 2H, J=7 Hz), 7.66(t, 2H, J=7.5 Hz), 3.91 (s, 3H). See Chuprakov et al., JACS, 2005, 127, 3714-3715.

Methyl 2-diazo-2-(4-(trifluoromethyl) phenyl) acetate (1-62n)

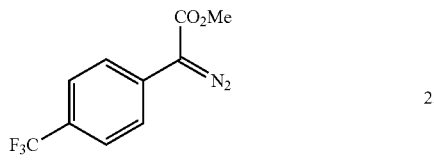

¹H NMR (500 MHz, CDCl₃): δ7.61 (s, 4H), 3.88 (s, 3H). See Rubina et al., Org. Lett., 2007, 9, 5501-5504.

Methyl 2-diazo-2-(3,5-(Bis trifluoromethyl) phenyl) acetate (1-62o)

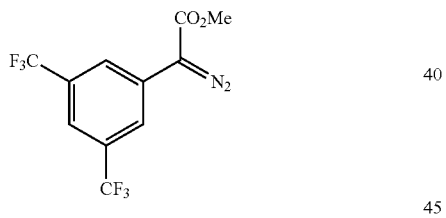

¹H NMR (500 MHz, CDCl₃): δ7.95 (s, 2H), 7.65 (s, 1H), 3.91 (s, 3H). See Lewis et al., J. Org. Chem., 2000, 65, 2615-2618

Methyl 2-([1,1'-biphenyl]-4-yl)-2-diazoacetate (1-62p)

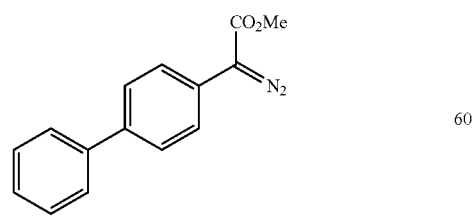

¹H NMR (400 MHz, CDCl₃) δ 3.90 (s, 3 H) 7.33-7.39 (m, 1 H) 7.45 (t, J=7.63 Hz, 2 H) 7.54-7.66 (m, 6 H).

Methyl 2-diazo-2-(naphthalene-2-yl) acetate (1-62q)

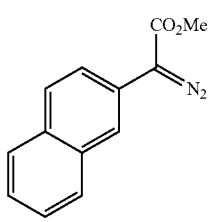

¹H NMR (400 MHz, CDCl₃) δ 3.92 (s, 3 H) 7.42-7.51 (m, 2 H) 7.54 (dd, J=8.80, 1.76 Hz, 1 H) 7.81 (d, J=8.22 Hz, 2 H) 7.86 (d, J=8.61 Hz, 1 H) 8.02 (s, 1 H).

1.4.2 Synthesis of RAL Acyclic Analogs

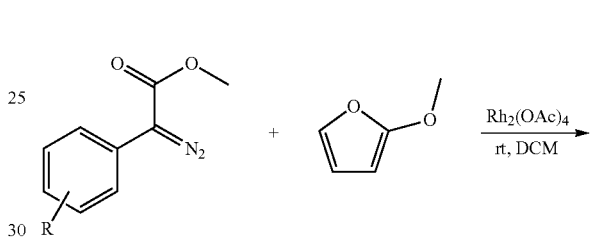

1-62

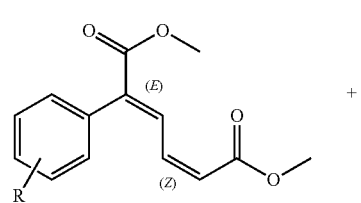

1-63
R = 4-Cl (93%) 4-OMe (82%)
4-Br (80%) 3,4-DiCl (94%)
4-I (93%) 3,4-DiOMe (99%)
4-NO₂ (91%) 3,5-DiCF₃ (83%)
4-CF₃ (81%) 3-OH (32%)
4-Ph (73%)

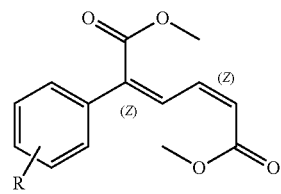

3,4-DiCl (2%)
4-Br (3%)
4-I (3%)
4-NO₂ (1%)

(2E, 4Z)dimethyl 2-(3,4-dichlorophenyl) hexa-2,4-dienedioate (1-63a)

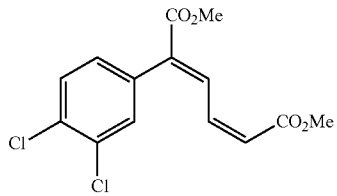

HDAB-001

88% Yield

A solution of methyl 2-diazo-2-(3,4-dichlorophenyl)cetate (244 mg, 1 mmol, 1 eq.) in hexanes (10 mL) was added by syringe pump over 2 h (mL/hr rate) to a solution of 2-methoxy furan (0.4 mL, 2 mmol, 2 eq.) and $Rh_2(OAc)_4$ (5 mg, 0.001 mmol, 0.01 eq.) in hexane (10 mL). The reaction mixture was stirred for an additional 1 h, and then concentrated in vacuo and purified by flash chromatography on silica gel using 9:1 hexane/Et2O as eluant to isolate colorless oily liquid, 276 mg (88%).

$^1$H NMR (500 MHz, $CDCl_3$): δ8.6 (d, 1H, J=12 Hz), 7.45 (d, 1H, J=8.0 Hz), 7.32 (s, 1H), 7.06 (dd, 1H, J=8.0 Hz), 6.52 (t, 1H, J=11.5 Hz), 5.94 (d, 1H, J=11.5 Hz), 3.81 (s, 3H), 3.78 (s, 3H). $^{13}$C NMR (300 MHz, $CDCl_3$): δ166.4, 165.7, 137.9, 136.8, 134.8, 133.8, 132.7, 132.3, 132.0, 130.0, 129.6, 124.8, 52.5, 51.6. IR ($CHCl_3$): 1717, 1437, 1200, 1175, 831 $cm^{-1}$. Anal. Calcd. for $C_{14}H_{12}Cl_2O_4$: C, 53.36; H, 3.84. Found: C, 53.38; H, 3.92.

(2E,4Z)-dimethyl 2-(4-methoxyphenyl) hexa-2,4-dienedioate (1-63b)

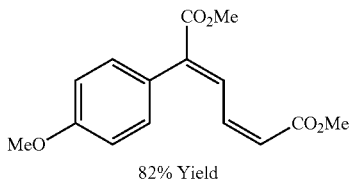

HDAB-002

82% Yield

A solution of methyl 2-diazo-2-(4-methoxyphenyl)acetate (412 mg, 2 mmol, 1 eq.) in hexanes (10 mL) was added by syringe pump over 2 h (5 mL/hr rate) to a solution of 2-methoxy furan (0.8 mL, 4 mmol, 2 eq.) and $Rh_2(OAc)_4$ (10 mg, 0.002 mmol, 0.01 eq.) in hexane (10 mL). The reaction mixture was stirred for an additional 1 h, and then concentrated in vacuo and purified by flash chromatography on silica gel using 9:1 hexane/Et2O as eluant to isolate colorless oily liquid, 452 mg (82%).

$^1$H NMR (500 MHz, $CDCl_3$): δ8.49 (d, 1H, J=11.5 Hz), 7.15 (dd, 2H, J=8.5 Hz), 6.89 (dd, 2H J=8.5 Hz), 6.63 (t, 1H, J=11.5 Hz), 5.84 (d, 1H, J=11.5 Hz), 3.80 (s, 3H), 3.79 (s, 3H), 3.76 (s, 3H). HRMS (EI) m/z calcd for $[C_{15}H_{16}O_5]^+$ 277.1071; Found: 277.1061.

(2E,4Z)-dimethyl 2-(3,4-dimethoxyphenyl) hexa-2,4-dienedioate (1-63c)

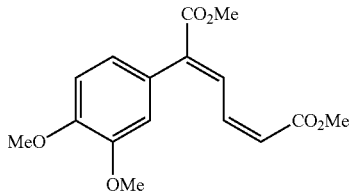

HDAB-003

99% Yield

A solution of methyl 2-diazo-2-(3,4-dimethoxyphenyl)acetate (472 mg, 2 mmol, 1 eq.) in hexanes (10 mL) was added by syringe pump over 2 h (5 mL/hr rate) to a solution of 2-methoxy furan (0.4 mL, 4 mmol, 2 eq.) and $Rh_2(OAc)_4$ (10 mg, 0.002 mmol, 0.01 eq.) in hexane (10 mL). The reaction mixture was stirred for an additional 1 h, and then concentrated in vacuo and purified by flash chromatography on silica gel using 1:1 hexane/$Et_2O$ as eluant to isolate yellow oily liquid, 605 mg (99%).

$^1$H NMR (500 MHz, $CDCl_3$): δ8.77 (d, 1H, J=11.7 Hz), 7.13 (d, 1H, J=8.7 Hz), 7.03 (d, 2H), 6.94 (t, 1H, J=11.4 Hz), 6.14 (d, 1H, J=11.4 Hz), 4.16 (s, 3H), 4.12 (s, 3H), 4.08 (s, 3H), 4.05 (s, 3H). $^{13}$CNMR (300 MHz, CDCl3): δ167.4(C), 166.0(C), 149.2(C), 148.3(C), 139.3(CH), 139.2(C), 133.2 (CH), 126.3(C), 123.2(CH), 123.0(CH), 113.4(CH), 110.5 (CH), 55.8($CH_3$), 55.7($CH_3$), 52.3($CH_3$), 51.4($CH_3$). HRMS (EI) m/z calcd for $[C_{16}H_{18}O_6]^+$ 306.1098; Found: 306.1100.

(2E,4Z)-dimethyl 2-(benzofuran-3-yl) hexa-2,4-dienedioate (1-63d)

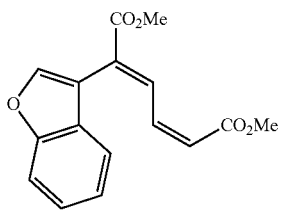

HDAB-004

88% Yield

A solution of methyl 2-(benzofuran-3-yl)-2-diazoethanoate (108 mg, 0.5 mmol, 1 eq.) in hexanes (10 mL) was added by syringe pump over 2 h (5 mL/hr rate) to a solution of 2-methoxy furan (0.1 mL, 1 mmol, 2 eq.) and $Rh_2(OAc)_4$ (3 mg, 0.005 mmol, 0.01 eq.) in hexane (10 mL). The reaction mixture was stirred for an additional 1h, and then concentrated in vacuo and purified by flash chromatography on silica gel using 8:1 hexane/$Et_2O$ as eluant to isolate colorless oily liquid, 126 mg (88%).

$^1$H NMR (500 MHz, $CDCl_3$): δ8.9 (d, 1H, J=12 Hz), 7.8(s, 1H), 7.72 (d, 1H, J=8.1 Hz), 7.57 (d, 1H, J=7.5 Hz), 7.54-7.43 (m, 2H), 6.96 (t, 1H, J=11.7 Hz), 6.1 (d, 1H, J=11.1 Hz), 4.03 (s, 3H), 3.99 (s, 3H). $^{13}$C-NMR (300 MHz, $CDCl_3$): δ166.6(C), 165.9(C), 154.8(C), 145.2(CH), 138.6 (CH), 135.2(CH), 129.3(C), 127.1(C), 124.6(CH), 123.6

(CH), 122.9(CH), 120.6(CH), 114.1(C), 111.5(CH), 52.4 (CH₃), 51.5(CH₃). HRMS (EI) m/z calcd for $[C_{16}H_{14}O_5]^+$ 286.0836; Found: 286.0840.

(2E,4Z)-dimethyl 2-(3-(tert-butyldimethylsilyloxy) phenyl) hexa-2,4-dienedioate (1-63g)

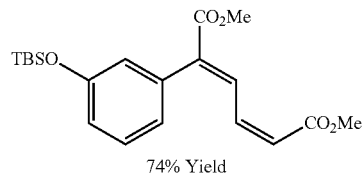 [SMILES: COC(=O)/C=C\C=C(\C(=O)OC)c1cccc(O[Si](C)(C)C(C)(C)C)c1]

74% Yield

A solution of methyl 2-(3-(tert-butyldimethylsilyloxy) phenyl)-2-diazoethanoate (613 mg, 2 mmol, 1 eq.) in hexanes (10 mL) was added by syringe pump over 2 h (5 mL/hr rate) to a solution of 2-methoxy furan (0.4 mL, 4 mmol, 2 eq.) and Rh₂(OAc)₄ (10 mg, 0.002 mmol, 0.01 eq.) in hexane (10 mL). The reaction mixture was stirred for an additional 1 h, and then concentrated in vacuo and purified by flash chromatography on silica gel using 5:1 hexane/Et₂O as eluant to isolate yellow oily liquid, 560 mg (74%).

¹H NMR (500 MHz, CDCl₃): δ8.54 (d, 1H, J=12 Hz), 7.28 (d, 1H, J=8.0 Hz), 6.88 (d, 1H J=8.0 Hz), 6.83 (d, 1H, J=8.0 Hz), 6.73 (s, 1H), 6.64(t, 1H, J=11.5 Hz), 5.90 (d, 1H, J=11.5 Hz), 3.83 (s, 3H), 3.82 (s, 3H), 1.00 (s, 9H), 0.22 (s, 6H), ¹³C-NMR(300 MHz, CDCl₃): δ166.9(C), 165.8(C), 155.0(C), 139.1(C), 138.9(CH), 134.9(C), 133.5(CH), 128.8 (CH), 123.3(CH), 123.1(CH), 121.9(CH), 120.0(CH), 52.1 (CH₃), 51.5(CH₃), 25.4(CH3), 17.99(C), −4.6(CH₃). HRMS (EI) m/z calcd for $[C_{20}H_{28}O_5Si]^+$ 399.1598; Found: 399.1614.

(2E,4Z)-dimethyl 2-(3-hydroxyphenyl) hexa-2,4-dienedioate (1-63e)

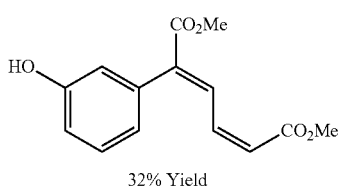

HDAB-005

32% Yield (2E,4Z)-dimethyl 2-(3-(tert-butyldimethylsilyloxy) phenyl) hexa-2,4-dienedioate (188 mg, 0.5 mmol, 1 eq.) was dissolved in THF (10 mL) and cooled to 0° C. Tetra n-butyl ammonium fluoride (0.55 mL, 0.55 mmol, 1.1 eq. (1M solution in THF)) was added slowly over a period of 1 hour. The reaction mixture was stirred for overnight, and then added water, extracted with dichloromethane, dried over MgSO₄ and concentrated in vacuo and purified by flash chromatography on silica gel using 9:1 hexane/Et₂O as eluant to isolate yellow oily liquid, 43 mg (32%).

¹H NMR (500 MHz, CDCl₃): δ8.73 (d, 1H, J=11.7 Hz), 7.4-7.39 (m, 1H), 7.00 (d, 1H, J=8.4 Hz), 6.93-6.78 (m, 3H), 6.0 (d, 1H, J=11.7 Hz), 4.00 (s, 3H), 3.98 (s, 3H). ¹³C NMR (300 MHz, CDCl₃): δ168.2, 166.8, 156.2, 139.6, 135.6, 134.5, 129.8, 124.1, 122.9, 117.7, 116.2, 53.1, 52.2.

(2Z,4E)-methyl 6-(4-methoxyphenyl)-6-oxohexa-2,4-dienoate (1-63f)

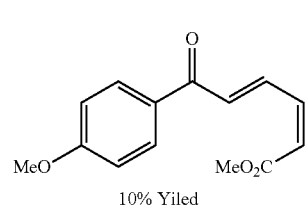

HDAB-006

10% Yiled

A solution of methyl 2-diazo-1-(4-methoxyphenyl) ethanone (176 mg, 1 mmol, 1 eq.) in hexanes (10 mL) was added by syringe pump over 2 h (5 mL/hr rate) to a solution of 2-methoxy furan (0.2 mL, 2 mmol, 2 eq.) and Rh₂(OAc)₄ (5 mg, 0.001 mmol, 0.01 eq.) in hexane (10 mL). The reaction mixture was stirred for an additional 1 h and then concentrated in vacuo and purified by flash chromatography on silica gel using 5:1 hexane/Et₂O as eluant to isolate oily liquid, 25 mg (10%).

¹H NMR (500 MHz, CDCl₃): δ8.43-8.34 (dd, 1H, J=12 Hz), 7.94 (d, 2H, J=9.0 Hz), 7.1 (d, 1H, J=15.3 Hz), 6.95 (d, 2H, J=8.7 Hz), 6.76 (t, 1H, J=11.4 Hz), 6.0 (d, 1H, J=11 Hz), 3.87 (s, 3H), 3.77 (s, 3H). ¹³C-NMR (300 MHz, CDCl₃): δ189.5(C), 166.3(C), 164.1(C), 141.8(CH), 138.0(CH), 133.6(CH), 131.5(CH), 131.0(C), 125.0(CH), 114.4(CH), 56.0(CH₃), 52.1(CH₃).

(2Z,4Z)-dimethyl 2-(3,4-dichlorophenyl) hexa-2,4-dienedioate (1-63i): Minor Isomer was Also Isolated.

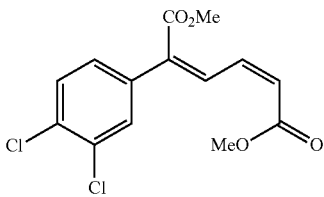

HDAB-007

2% Yield

¹H NMR (500 MHz, CDCl₃): δ8.10 (d, 1H, J=12 Hz), 7.52 (s, 1H), 7.43 (d, 1H, J=8.5 Hz), 7.27 (d, 1H, J=9 Hz), 7.17 (t, 1H, J=11.5 Hz), 5.97 (d, 1H, J=11.5 Hz), 3.88 (s, 3H), 3.76 (s, 3H). ¹³C-NMR (300 MHz, CDCl₃): δ166.9(C), 166.1(C), 138.6(CH), 137.8(C), 136.4(C), 133.0(C), 132.7 (C), 130.5(CH), 130.4(CH), 129.3(CH), 126.8(CH), 122.6 (CH), 52.45(CH₃), 51.54(CH₃).

(2E,4E)-dimethyl 2-(3,4-dichlorophenyl) hexa-2,4-dienedioate (1-63j)

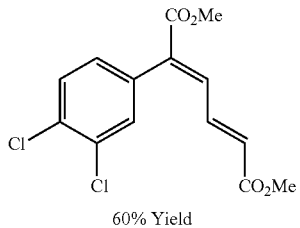

60% Yield (2E,4Z)-dimethyl 2-(3,4-dichlorophenyl) hexa-2,4-dienedioate (31 mg, 0.1 mmol, 1 eq.) was dissolved in THF (1 mL) and then iodine (3 mg, 0.01 mmol, 0.1 eq.) at rt. The reaction mixture was stirred was stirred for an additional 1 h, and then concentrated in vacuo and purified by flash chromatography on silica gel using 8:1 hexane/Et$_2$O as eluant to isolate oily liquid, 6 mg (60%).

$^1$H NMR (500 MHz, CDCl$_3$): δ7.50 (t, 2H, J=12 Hz, 8.5 Hz), 7.33 (d, 1H, J=2 Hz), 7.15(dd, 1H, J=12 Hz, 3.5 Hz), 7.06 (dd, 1H, J=8 Hz, 1.5 Hz), 6.28 (d, 1H, J=15.5 Hz), 3.80 (s, 3H), 3.74 (s, 3H). $^{13}$C NMR (300 MHz, CDCl$_3$): δ166.2 (C), 166.1(C), 138.3(CH), 137.7(CH), 136.8(C), 133.7(C), 133.0(C), 132.5(C), 131.8(CH), 130.2(CH), 129.4(CH), 129.1(CH), 52.73(CH$_3$), 51.9(CH$_3$). IR (CHCl$_3$): 1716, 1236 cm$^{-1}$.

(2E,4Z)-dimethyl 2-(4-chlorophenyl) hexa-2,4-dienedioate (1-63k)

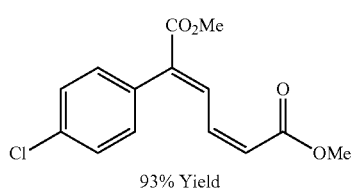

93% Yield

A solution of methyl 2-(4-chlorophenyl)-2-diazoacetate (631 mg, 3 mmol, 1 eq.) in hexanes (25 mL) was added by syringe pump over 2.5 h (10 mL/hr rate) to a solution of 2-methoxy furan (0.6 mL, 6 mmol, 2 eq.) and Rh$_2$(OAc)$_4$ (15 mg, 0.003 mmol, 0.01 eq.) in hexane (25 mL). The reaction mixture was stirred for an additional 1 h, and then concentrated in vacuo and purified by flash chromatography on silica gel using 8:1 hexane/Et$_2$O as eluant to isolate oily liquid, 789 mg (93%).

$^1$H NMR (500 MHz, CDCl$_3$): δ8.59 (d, 1H, J=12 Hz), 7.32(d, 2H, J=8.5 Hz), 7.17 (d, 2H J=8.5 Hz), 6.56 (t, 1H J=11.5 Hz), 5.91 (d, 1H, J=11.5 Hz), 3.82 (s, 3H), 3.79 (s, 3H). $^{13}$C-NMR (300 MHz, CDCl$_3$): δ166.9(C), 165.9(C), 138.5(CH), 138.2(C), 134.5(C), 134.1(CH), 132.3(C), 131.6 (CH), 128.3(CH), 124.1(CH), 52.53(CH$_3$), 51.64(CH$_3$). IR (CHCl$_3$): 1717, 1437, 1244, 1200, 1175, 1014, 831 cm$^{-1}$. HRMS (EI) m/z calcd for [C$_{14}$H$_{13}$O$_4$Cl$_1$]$^+$ 280.0497; Found: 280.0500. Anal. Calcd. for C$_{14}$H$_{13}$O$_4$Cl$_1$: C, 59.90; H, 4.67. Found: C, 60.15; H, 4.63.

(2E,4Z)-dimethyl 2-(4-bromophenyl) hexa-2,4-dienedioate (1-63l)

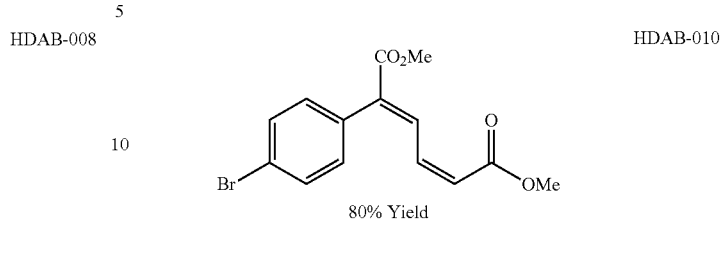

80% Yield

A solution of methyl 2-(4-bromophenyl)-2-diazoacetate (765 mg, 3 mmol, 1 eq.) in hexanes (25 mL) was added by syringe pump over 2.5 h (10 mL/hr rate) to a solution of 2-methoxy furan (0.6 mL, 6 mmol, 2 eq.) and Rh$_2$(OAc)$_4$ (15 mg, 0.003 mmol, 0.01 eq.) in hexane (25 mL). The reaction mixture was stirred for an additional 1h, and then concentrated in vacuo and purified by flash chromatography on silica gel using 8:1 hexane/Et$_2$O as eluant to isolate oily liquid, 747 mg (80%).

$^1$H NMR (500 MHz, CDCl$_3$): δ8.58 (d, 1H, J=12 Hz), 7.53(d, 2H, J=8 Hz), 7.10 (d, 2H J=8 Hz), 6.56 (t, 1H J=11.5 Hz), 5.91 (d, 1H, J=11.5 Hz), 3.81 (s, 3H), 3.79 (s, 3H). $^{13}$C NMR (300 MHz, CDCl$_3$): δ166.8(C), 165.8(C), 138.4(CH), 138.2(C), 134.1(CH), 132.7(C), 131.9(CH), 131.2(CH), 124.1(CH), 122.7(C), 52.48(CH3), 51.60(CH3). IR (CHCl$_3$): 2951, 1719, 1626, 1578, 1437, 1244, 1011, 830 cm$^{-1}$. HRMS (EI) m/z calcd for [C$_{14}$H$_{13}$O$_4$Br$_1$]$^+$ 323.9992; Found: 323.9996. Anal. Calcd. for C$_{14}$H$_{13}$O$_4$Br$_1$: C, 51.71; H, 4.03. Found: C, 52.02; H, 4.04.

(2E,4Z)-dimethyl 2-(4-iodophenyl) hexa-2,4-dienedioate (1-63m)

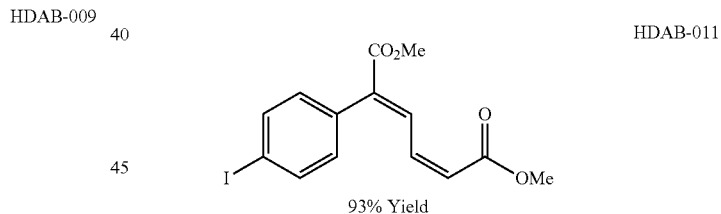

93% Yield

A solution of methyl 2-diazo-2-(4-iodophenyl) acetate (906 mg, 3 mmol, 1 eq.) in hexanes (25 mL) was added by syringe pump over 2.5 h (10 mL/hr rate) to a solution of 2-methoxy furan (0.6 mL, 6 mmol, 2 eq.) and Rh$_2$(OAc)$_4$ (15 mg, 0.003 mmol, 0.01 eq.) in hexane (25 mL). The reaction mixture was stirred for an additional 1 h, and then concentrated in vacuo and purified by flash chromatography on silica gel using 8:1 hexane/Et$_2$O as eluant to isolate oily liquid, 1.046 g (93%).

$^1$H NMR (500 MHz, CDCl$^3$): δ8.57 (d, 1H, J=11.5 Hz), 7.73(d, 2H, J=8 Hz), 6.97 (d, 2H J=8.5 Hz), 6.56 (t, 1H J=11.5 Hz), 5.91 (d, 1H, J=11.5 Hz), 3.81 (s, 3H), 3.79 (s, 3H). $^{13}$C NMR (300 MHz, CDCl$_3$): δ166.9(C), 165.9(C), 138.6(CH), 138.3(C), 137.2(CH), 134.2(CH), 133.4(C), 132.1(CH), 124.2(CH), 52.6(CH$_3$), 51.7(CH$_3$). IR (CHCl$_3$): 1715, 1434, 1237, 1201, 1166, 1006 cm$^{-1}$. HRMS (EI) m/z calcd for [C$_{14}$H$_{13}$O$_4$I$_1$]$^+$ 371.9853; Found: 371.9854. Anal. Calcd. for C$_{14}$H$_{13}$O$_4$I$_1$: C, 45.18; H, 3.52. Found: C, 45.47; H, 3.54.

(2E,4Z)-dimethyl 2-(4-nitrophenyl) hexa-2,4-dienedioate (1-63n)

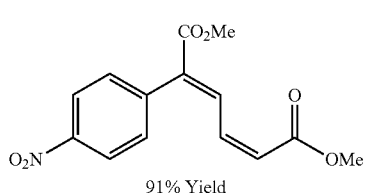

HDAB-012

91% Yield

A solution of methyl 2-diazo-2-(4-nitrophenyl) acetate (663 mg, 3 mmol, 1 eq.) in hexanes (25 mL) was added by syringe pump over 2.5 h (10 mL/hr rate) to a solution of 2-methoxy furan (0.6 mL, 6 mmol, 2 eq.) and $Rh_2(OAc)_4$ (5 mg, 0.003 mmol, 0.01 eq.) in hexane (25 mL). The reaction mixture was stirred for an additional 1h, and then concentrated in vacuo and purified by flash chromatography on silica gel using 8:1 hexane/$Et_2O$ as eluant to isolate colorless oily liquid, 796 mg (91%).

$^1$H NMR (500 MHz, $CDCl_3$): δ8.71 (d, 1H, J=12 Hz), 8.26(d, 2H, J=8.5 Hz), 7.43 (d, 2H J=9 Hz), 6.50 (t, 1H J=11.5 Hz), 5.99 (d, 1H, J=11.5 Hz), 3.84 (s, 3H), 3.81 (s, 3H). $^{13}$C NMR (300 MHz, $CDCl_3$): δ166.2(C), 165.6(C), 147.6(C), 140.6(C), 137.4(CH), 136.9(C), 135.2(CH), 131.3 (CH), 125.3(CH), 123.18(CH), 52.6($CH_3$), 51.7($CH_3$). IR ($CHCl_3$): 1718, 1519, 1437, 1350, 1246, 1202, 1176 cm−1. HRMS (EI) m/z calcd for $[C_{14}H_{13}O_6N_1]^+$ 291.0737; Found: 291.0738.

(2E,4Z)-dimethyl 2-(4-(trifluoromethyl) phenyl) hexa-2,4-dienedioate (1-63o)

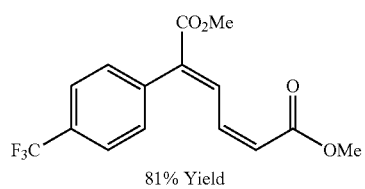

HDAB-013

81% Yield

A solution of methyl 2-diazo-2-(4-(trifluoromethyl) phenyl) acetate (244 mg, 1 mmol, 1 eq.) in hexanes (10 mL) was added by syringe pump over 1 h (10 mL/hr rate) to a solution of 2-methoxy furan (0.2 mL, 2 mmol, 2 eq.) and $Rh_2(OAc)_4$ (5 mg, 0.001 mmol, 0.01 eq.) in hexane (10 mL). The reaction mixture was stirred for an additional 1 h, and then concentrated in vacuo and purified by flash chromatography on silica gel using 8:1 hexane/$Et_2O$ as eluant to isolate colorless oily liquid, 254 mg (81%).

$^1$H NMR (500 MHz, $CDCl_3$): δ8.65 (d, 1H, J=12 Hz), 7.66(d, 2H, J=7.5 Hz), 7.36 (d, 2H J=7 Hz), 6.51 (t, 1H J=11.5 Hz), 5.93 (d, 1H, J=11.5 Hz), 3.83 (s, 3H), 3.80 (s, 3H). $^{13}$C NMR (300 MHz, $CDCl_3$): δ166.7(C), 165.8(C), 138.1(CH), 137.9(C), 137.6(C), 134.7(CH), 130.6(CH), 125.0(CH), 124.7(CH), 52.6($CH_3$), 51.7($CH_3$). IR ($CHCl_3$): 1720, 1325, 1246, 1201, 1176, 1128, 1111, 1067 cm$^{-1}$. HRMS (EI) m/z calcd for $[C_{15}H_{13}O_4F_3]^+$ 314.0760; Found: 314.0755. Anal. Calcd. for $C_{15}H_{13}O_4F_3$: C, 57.33; H, 4.17. Found: C, 57.57; H, 4.19.

(2E,4Z)-dimethyl 2-(3,5-(bis trifluoromethyl) phenyl) hexa-2,4-dienedioate (1-63p)

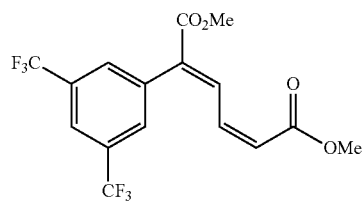

HDAB-014

83% Yield

A solution of methyl 2-diazo-2-(3,5-(Bis trifluoromethyl) phenyl) acetate (312 mg, 1 mmol, 1 eq.) in hexanes (10 mL) was added by syringe pump over 1 h (10 mL/hr rate) to a solution of 2-methoxy furan (0.2 mL, 2 mmol, 2 eq.) and $Rh_2(OAc)_4$ (5 mg, 0.001 mmol, 0.01 eq.) in hexane (10 mL). The reaction mixture was stirred for an additional 1 h, and then concentrated in vacuo and purified by flash chromatography on silica gel using 8:1 hexane/$Et_2O$ as eluant to isolate colorless oily liquid, 317 mg (83%).

$^1$H NMR (500 MHz, $CDCl_3$): δ8.73 (d, 1H, J=11.5 Hz), 8.56(s, 1H), 8.16 (s, 1H), 7.90 (s, 1H), 6.44 (t, 1H, J=11.5 Hz), 6.01 (d, 1H, J=11.5 Hz), 3.85 (s, 3H), 3.81 (s, 3H). IR ($CHCl_3$): 1721, 1281, 1171, 1137 cm$^{-1}$. HRMS (EI) m/z calcd for $[C_{16}H_{12}O_4F_6]^+$ 382.0634; Found: 382.0638.

(2Z,4Z)-dimethyl 2-(4-bromophenyl) hexa-2,4-dienedioate (1-63q): Minor Isomer was Also Isolated.

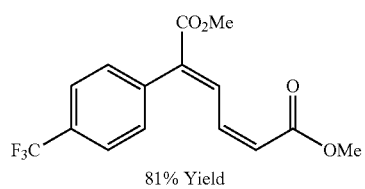

HDAB-015

3% Yiled $^1$H NMR (500 MHz, $CDCl_3$): δ8.11 (d, 1H, J=11.5 Hz), 7.49(d, 2H, J=7.5 Hz), 7.31 (d, 2H J=7.5 Hz), 7.13 (t, 1H J=12 Hz), 5.94 (d, 1H, J=11.5 Hz), 3.87 (s, 3H), 3.75 (s, 3H).

(2Z,4Z)-dimethyl 2-(4-iodophenyl) hexa-2,4-dienedioate (1-63r): Minor Isomer was Also Isolated.

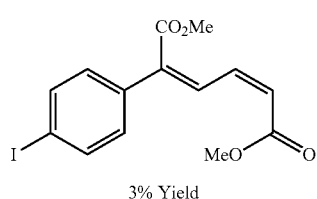

HDAB-016

3% Yield $^1$H NMR (500 MHz, $CDCl_3$): δ8.10 (d, 1H, J=11.5 Hz), 7.70(d, 2H, J=7.5 Hz), 7.17 (d, 2H J=7 Hz), 7.13 (t, 1H J=11.5 Hz), 5.95 (d, 1H, J=11.5 Hz), 3.87 (s, 3H), 3.79 (s, 3H). $^{13}$C NMR (300 MHz, CDCl$_3$): δ167.4(C), 166.2(C), 139.4(C), 139.0(CH), 138.2(C), 137.6(CH), 135.8(C), 129.1 (CH), 121.9(CH), 52.3(CH$_3$), 51.4(CH$_3$)

(2Z,4Z)-dimethyl 2-(4-nitrophenyl) hexa-2,4-dienedioate ((1-63s): Minor Isomer was Also Isolated.

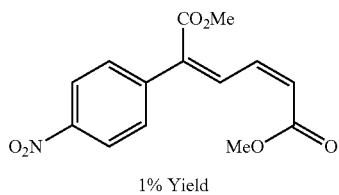

HDAB-017

1% Yield $^1$H NMR (500 MHz, CDCl$_3$): δ8.23 (d, 2H, J=8.5 Hz), 8.21(d, 1H, J=12 Hz), 7.60 (d, 2H J=8.5 Hz), 7.26 (t, 1H J=12 Hz), 6.04 (d, 1H, J=11 Hz), 3.89 (s, 3H), 3.77 (s, 3H).

(2E,4Z)-methyl 2-(3-(tert-butyldimethylsilyloxy) phenyl)-6-oxohepta-2,4-dienoate (1-63f)

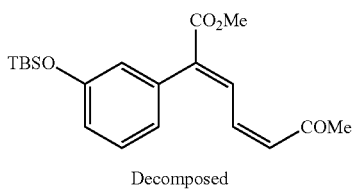

Decomposed

A solution of methyl 2-(3-(tert-butyldimethylsilyloxy) phenyl)-2-diazoethanoate (306 mg, 1 mmol, 1 eq.) in hexanes (10 mL) was added by syringe pump over 3 h (5 mL/hr rate) to a solution of 2-methoxy furan (0.2 mL, 2 mmol, 2 eq.) and Rh$_2$(OAc)$_4$ (5 mg, 0.001 mmol, 0.01 eq.) in hexane (10 mL). The reaction mixture was stirred for an additional 1 h, and then concentrated in vacuo and purified by flash chromatography on silica gel using 5:1 hexane/Et$_2$O as eluant to isolate oily liquid, 130 mg (36%). Product decomposed at room temperature after isolation.

$^1$H NMR (500 MHz, CDCl$_3$): δ8.39 (d, 1H, J=11.5 Hz), 7.23 (t, 1H, J=7.5 Hz), 6.86 (d, 1H J=7 Hz), 6.8 (d, 1H, J=7.5 Hz), 6.70 (s, 1H), 6.44(t, 1H, J=11.5 Hz), 6.21 (d, 1H, J=11.5 Hz), 3.83 (s, 3H), 2.29 (s, 3H), 0.97 (s, 9H), 0.19 (s, 6H). $^{13}$C NMR (300 MHz, CDCl$_3$): δ198.5(C), 167.1(C), 155.1(C), 139.7(C), 136.3(CH), 135.0(C), 134.2(CH), 130.3(CH), 128.8(CH), 123.2(CH), 121.9(CH), 120.0(CH), 52.2(CH$_3$), 31.46(CH$_3$), 25.5(CH$_3$), 18.0(C), 4.5(CH$_3$). HRMS (EI) m/z calcd for [C$_{20}$H$_{28}$O$_4$Si]$^+$ 383.1649; Found: 383.1642.

(2Z,4E)-methyl 5-(3,4-dichlorophenyl)-6-(methoxy (methyl) amino)-6-oxohexa-2,4-dienoate (1-63h)

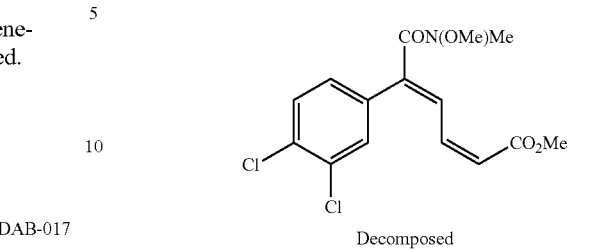

Decomposed

A solution of 2-diazo-2-(3,4-dichlorophenyl)-N-methoxy-N-methylacetamide (27.41 mg, 0.1 mmol, 1 eq.) in hexanes (5 mL) was added by syringe pump over 1 h (5 mL/hr rate) to a solution of 2-methoxy furan (0.02 mL, 0.2 mmol, 2 eq.) and Rh2(OAc)4(1 mg, 0.001 mmol, 0.01 eq.) in hexane (5 mL). The reaction mixture was stirred for an additional 1 h, and then concentrated in vacuo. Purified by flash chromatography on silica gel using 5:1 hexane/Et$_2$O as eluant to isolate colorless oily liquid, 30 mg (88%). Product decomposed at room temperature after isolation.

1H NMR (500 MHz, CDCl3): δ7.80 (d, 1H, J=11.5 Hz), 7.48 (m, 3H), 6.66 (t, 1H, J=11.5 Hz), 5.91 (d, 1H, J=11.5 Hz), 3.76 (s, 3H), 3.48 (s, 3H), 3.23 (s, 3H).

(2E,4Z)-1-ethyl 6-methyl 2-(3,4-dibromophenyl) hexa-2,4-dienedioate

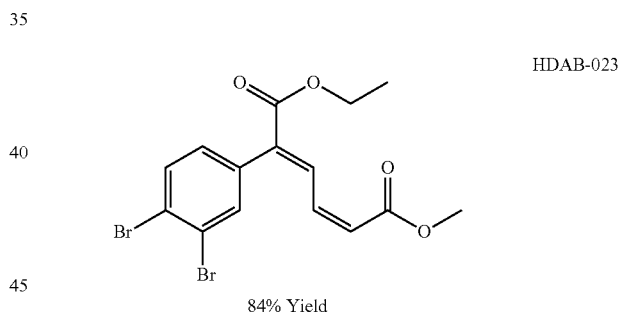

HDAB-023

84% Yield

A solution of ethyl 2-diazo-2-(3,4-dibromophenyl)acetate (345 mg, 1 mmol, 1 eq.) in hexanes (10 mL) was added by syringe pump over 2 h (5 mL/hr rate) to a solution of 2-methoxy furan (0.2 mL, 2 mmol, 2 eq.) and Rh$_2$(OAc)$_4$ (5 mg, 0.002 mmol, 0.01 eq.) in hexane (10 mL). The reaction mixture was stirred for an additional 1 h, and then concentrated in vacuo and purified by flash chromatography on silica gel using 9:1 hexane/Et$_2$O as eluant to isolate colorless oily liquid, 339 mg (84%).

$^1$H NMR (400 MHz, CDCl$_3$) δ 1.33 (t, J=7.02 Hz, 3 H) 3.80 (s, 3 H) 4.29 (q, J=7.02 Hz, 2 H) 5.30 (s, 1 H) 5.95 (dd, J=11.59, 0.92 Hz, 1 H) 6.55 (t, J=11.59 Hz, 1 H) 7.05 (dd, J=8.09, 1.98 Hz, 1 H) 7.51 (d, J=1.83 Hz, 1 H) 7.64 (d, J=8.24 Hz, 1 H) 8.55-8.66 (m, 1 H) $^{13}$C NMR (75 MHz, CDCl$_3$) δ 14.1, 51.6, 61.5, 124.4, 124.6, 124.9, 130.3, 133.1, 134.4, 134.5, 135.0, 137.0, 137.9, 165.7, 165.8. FT-IR (neat): 1708, 1461, 1195, 1172,827 cm$^{-1}$; HRMS (pos-APCI) calcd for C$_{15}$H$_{14}$O$_4$Br$_2$: 415.92643 Found: 415.92656.

(2E,4Z)-dimethyl 2-(3,4-dibromophenyl)hexa-2,4-dienedioate (HDAB-022) was similarly made substituting the appropriate starting material.

(2E,4Z)-1-isopropyl 6-methyl 2-(3,4-dibromophenyl)hexa-2,4-dienedioate

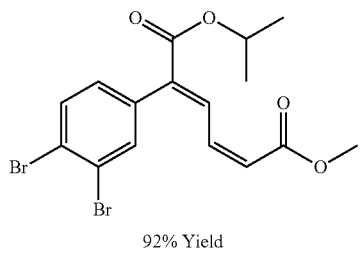

HDAB-024

92% Yield

A solution of isopropyl 2-diazo-2-(3,4-dibromophenyl)acetate (360 mg, 1 mmol, 1 eq.) in hexanes (10 mL) was added by syringe pump over 2 h (5 mL/hr rate) to a solution of 2-methoxy furan (0.2 mL, 2 mmol, 2 eq.) and $Rh_2(OAc)_4$ (5 mg, 0.002 mmol, 0.01 eq.) in hexane (10 mL). The reaction mixture was stirred for an additional 1 h, and then concentrated in vacuo and purified by flash chromatography on silica gel using 9:1 hexane/$Et_2O$ as eluant to isolate colorless oily liquid, 395 mg (92%).

$^1$H NMR (400 MHz, $CDCl_3$) δ 1.31 (d, J=5.19 Hz, 6 H) 3.80 (br. s., 3 H) 5.07-5.22 (m, 1 H) 5.94 (d, J=11.29 Hz, 1 H) 6.55 (t, J=11.75 Hz, 1 H) 7.04 (d, J=8.24 Hz, 1 H) 7.50 (s, 1 H) 7.60-7.69 (m, 1 H) 8.56 (d, J=11.59 Hz, 1 H); $^{13}$C NMR (75 MHz, $CDCl_{13}$) δ 21.6, 51.6, 69.2, 124.4, 124.5, 124.8, 130.4, 133.1, 134.2, 134.7, 135.1, 137.4, 138.0, 165.4, 165.7; FT-IR (neat): 1705, 1436, 1196, 1172, 1104, 009, 826 cm$^{-1}$; HRMS (pos-APCI) calcd for $C_{16}H_{16}O_4Br_2$: 429.94208 Found: 429.94208.

(2E,4Z)-methyl 2-(3,4-dichlorophenyl)-6-oxohepta-2,4-dienoate

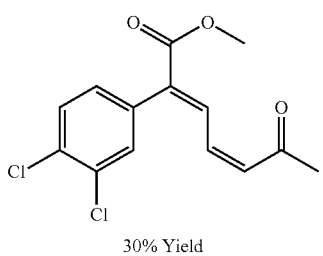

HDAB-025

30% Yield

A solution of methyl 2-diazo-2-(3,4-dichlorophenyl)acetate (244 mg, 1 mmol, 1 eq.) in hexanes (10 mL) was added by syringe pump over 2 h (5 mL/hr rate) to a solution of 2-methyl furan (164 mg, 2 mmol, 2 eq.) and $Rh_2(OAc)_4$ (5 mg, 0.002 mmol, 0.01 eq.) in hexane (10 mL). The reaction mixture was stirred for an additional 1 h, and then concentrated in vacuo and purified by flash chromatography on silica gel using 9:1 hexane/$Et_2O$ as eluant to isolate colorless oily liquid, 274 mg (92%).

$^1$H NMR (400 MHz, $CDCl_3$-d) δ 1.63 (s, 3 H) 3.13 (s, 3 H) 5.60-5.75 (m, 2 H) 6.41 (dd, J=8.09, 1.68 Hz, 1 H) 6.66 (d, J=1.53 Hz, 1 H) 6.79 (d, J=8.24 Hz, 1 H) 7.78 (d, J=11.29 Hz, 1 H); $^{13}$C NMR (75 MHz, $CDCl_3$) δ 31.3, 52.3, 129.5, 129.8, 131.4, 131.8, 131.9, 132.4, 133.7, 134.8, 135.4, 136.9, 166.2, 198.2; FT-IR (neat): 1712, 1686, 1434, 1236, 1174, 1030, 761 cm$^{-1}$; HRMS (neg-APCI) calcd for $C_{14}H_{12}O_3Cl_2$: 298.01690 Found: 298.01693.

(2E,4Z)-2-(3,4-dichlorophenyl)hexa-2,4-dienedioic acid

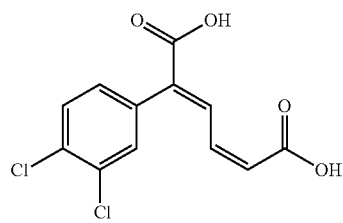

HDAB-026

90% Yield $^1$H NMR (400 MHz, ACETONE-$d_6$) δ 6.05 (d, J=11.59 Hz, 1 H) 6.67 (t, J=11.75 Hz, 1 H) 7.27 (dd, J=8.24, 1.83 Hz, 1 H) 7.52 (d, J=1.83 Hz, 1 H) 7.63 (d, J=8.24 Hz, 1 H) 8.72 (d, J=12.20 Hz, 1 H) $^{13}$C NMR (75 MHz, $CDCl_3$) δ 126.4, 131.0, 131.4, 132.3, 132.6, 133.1, 135.7, 136.0, 137.8, 138.9, 166.8, 167.4; FT-IR (neat): cm$^{-1}$; HRMS (pos-APCI) calcd for $C_{12}H_7O_4Cl_2$: 240.98286 Found: 240.98288.

(2E,4Z)-dimethyl 2-(naphthalen-2-yl)hexa-2,4-dienedioate

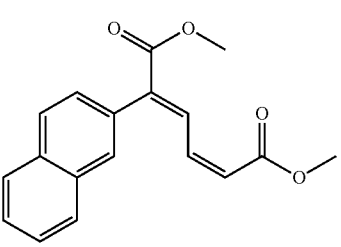

HDAB-028

79% Yield

A solution of methyl 2-diazo-2-(naphthalen-2-yl)acetate (226 mg, 1 mmol, 1 eq.) in hexanes (10 mL) was added by syringe pump over 2 h (5 mL/hr rate) to a solution of 2-methoxy furan (0.2 mL, 2 mmol, 2 eq.) and $Rh_2(OAc)_4$ (5 mg, 0.002 mmol, 0.01 eq.) in hexane (10 mL). The reaction mixture was stirred for an additional 1 h, and then concentrated in vacuo, and purified by flash chromatography on silica gel using 9:1 hexane/$Et_2O$ as eluant to isolate colorless oily liquid, 233 mg (79%).

$^1$H NMR (400 MHz, $CDCl_3$-d) δ 3.81 (s, 3 H) 3.83 (s, 3 H) 5.88 (d, J=11.59 Hz, 1 H) 6.64 (t, J=11.59 Hz, 1 H) 7.35 (dd, J=8.39, 1.37 Hz, 1 H) 7.47-7.59 (m, 2 H) 7.68 (s, 1 H) 7.86 (d, J=8.85 Hz, 4 H) 8.65 (d, J=11.90 Hz, 1 H); $^{13}$C NMR (75 MHz, $CDCl^3$) δ 51.3, 52.2, 123.5, 126.1, 126.4, 127.4, 127.4, 127.4, 127.8, 129.6, 131.2, 132.5, 132.7, 133.8, 138.8, 139.2, 165.7, 167.1; FT-IR (neat): 1711, 1434, 1194, 1174, 730 cm−1; FIRMS (neg-APCI) calcd for C18H16O4: 296.10541 Found: 296.10544.

(2E,4Z)-dimethyl 2-(benzofuran-3-yl)hexa-2,4-dienedioate

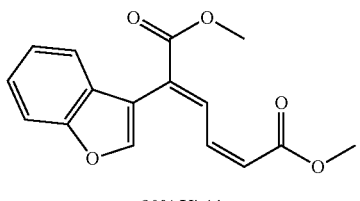

HDAB-029

90% Yield

A solution of methyl 2-(benzofuran-3-yl)-2-diazoacetate (216 mg, 1 mmol, 1 eq.) in hexanes (10 mL) was added by syringe pump over 2 h (5 mL/hr rate) to a solution of 2-methoxy furan (0.2 mL, 2 mmol, 2 eq.) and $Rh_2(OAc)_4$ (5 mg, 0.002 mmol, 0.01 eq.) in hexane (10 mL). The reaction mixture was stirred for an additional 1 h, and then concentrated in vacuo and purified by flash chromatography on silica gel using 9:1 hexane/$Et_2O$ as eluant to isolate colorless oily liquid, 257 mg (90%).

$^1$H NMR (400 MHz, $CDCl_3$-d) δ 3.83 (s, 3 H) 3.84 (s, 3 H) 5.29 (s, 1 H) 5.92 (d, J=11.29 Hz, 1 H) 6.78 (t, J=11.59 Hz, 1 H) 7.21-7.30 (m, 1 H) 7.30-7.43 (m, 2 H) 7.53 (d, J=8.24 Hz, 1 H) 7.69 (s, 1 H) 8.69 (d, J=11.90 Hz, 1 H); $^{13}$C NMR (75 MHz, $CDCl_3$) δ 51.4, 52.3, 53.3, 111.4, 114.1, 120.6, 122.9, 123.6, 124.5, 127.1, 129.2, 135.2, 138.6, 145.2, 145.2, 154.8, 165.8, 166.6; FT-IR (neat): 1712, 1451, 1435, 1195, 1173, 744 cm$^{-1}$; HRMS (neg-APCI) calcd for $C_{16}H_{14}O_5$: 286.08467 Found: 286.08469.

(2E,4Z)-dimethyl 2-(3-chloro-4-iodophenyl)hexa-2,4-dienedioate

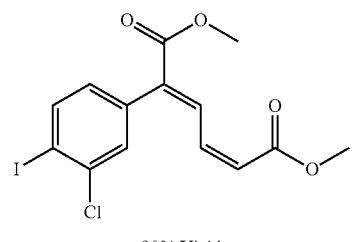

HDAB-030

90% Yield

A solution of methyl 2-(3-chloro-4-iodophenyl)-2-diazoacetate (335 mg, 1 mmol, 1 eq.) in hexanes (10 mL) was added by syringe pump over 2 h (5 mL/hr rate) to a solution of 2-methoxy furan (0.2 mL, 2 mmol, 2 eq.) and $Rh_2(OAc)_4$ (5 mg, 0.002 mmol, 0.01 eq.) in hexane (10 mL). The reaction mixture was stirred for an additional 1 h, and then concentrated in vacuo and purified by flash chromatography on silica gel using 9:1 hexane/$Et_2O$ as eluant to isolate colorless oily liquid, 364 mg (90%).

1H NMR (400 MHz, CDCl3-d) δ 3.80 (s, 3 H) 3.82 (s, 3 H) 5.95 (d, J=11.29 Hz, 1 H) 6.54 (t, J=11.59 Hz, 1 H) 7.16 (dd, J=8.24, 1.83 Hz, 1 H) 7.47 (d, J=8.24 Hz, 1 H) 7.72 (d, J=1.83 Hz, 1 H) 8.60 (d, J=11.90 Hz, 1 H); 13C NMR (75 MHz, CDCl3) δ 51.7, 52.6, 97.7, 124.7, 128.7, 131.3, 133.8, 134.7, 136.5, 137.9, 138.7, 141.4, 165.7, 166.5; FT-IR (neat): 1708, 1231, 1199, 1167, 729 cm−1; HRMS (neg-APCI) calcd for $C_{14}H_{11}O_4Cl1I1$: 404.93961 Found: 404.93978.

(2E,4Z)-methyl 2-(3,4-dichlorophenyl)-7,7-dimethyl-6-oxoocta-2,4-dienoate

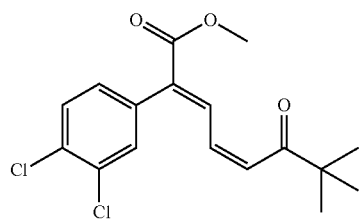

HDAB-031

18% Yield

A solution of methyl 2-diazo-2-(3,4-dichlorophenyl)acetate (244 mg, 1 mmol, 1 eq.) in hexanes (10 mL) was added by syringe pump over 2 h (5 mL/hr rate) to a solution of 2-(tert-butoxy)furan (280 mg, 2 mmol, 2 eq.) and $Rh_2(OAc)_4$ (5 mg, 0.002 mmol, 0.01 eq.) in hexane (10 mL). The reaction mixture was stirred for an additional 1 h, and then concentrated in vacuo, and purified by flash chromatography on silica gel using 9:1 hexane/$Et_2O$ as eluant to isolate colorless oily liquid, 61 mg (18%).

$^1$H NMR (400 MHz, $CDCl_3$-d) δ 1.19 (s, 9 H) 3.82 (s, 3 H) 6.37-6.51 (m, 1 H) 6.57 (d, J=11.59 Hz, 1 H) 7.08 (d, J=8.24 Hz, 1 H) 7.34 (s, 1 H) 7.47 (d, J=8.24 Hz, 1 H) 8.41 (d, J=11.59 Hz, 1 H); $^{13}$C NMR (75 MHz, $CDCl_3$) δ 26.1, 44.0, 52.5, 128.3, 129.7, 129.9, 132.0, 132.2, 132.6, 134.0, 135.9, 136.7, 166.6, 206.0; FT-IR (neat): 1713, 1681, 1473, 1236, 1067 cm$^{-1}$; HRMS (neg-APCI) calcd for $C_{17}H_{18}O_3Cl_2$: 340.06385 Found: 340.06391.

(2E,4Z)-dimethyl 2-(1-(tert-butoxycarbonyl)-1H-indol-3-yl)hexa-2,4-dienedioate

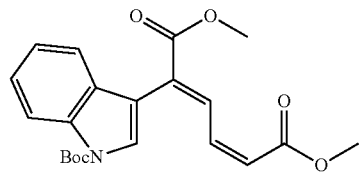

HDAB-032

48% Yield

A solution of tert-butyl 3-(1-diazo-2-methoxy-2-oxoethyl)-1H-indole-1-carboxylate (315 mg, 1 mmol, 1 eq.) in hexanes (10 mL) was added by syringe pump over 2 h (5 mL/hr rate) to a solution of 2-methoxy furan (0.2 mL, 2 mmol, 2 eq.) and $Rh_2(OAc)_4$ (5 mg, 0.002 mmol, 0.01 eq.) in hexane (10 mL). The reaction mixture was stirred for an additional 1 h, and then concentrated in vacuo and purified by flash chromatography on silica gel using 9:1 hexane/$Et_2O$ as eluant to isolate colorless oily liquid, 184 mg (48%).

$^1$H NMR (400 MHz, $CDCl_3$-d) δ 1.59-1.79 (m, 9 H) 3.80 (s, 3 H) 3.83 (s, 3 H) 5.88 (d, J=11.59 Hz, 1 H) 6.74 (t, J=11.59 Hz, 1 H) 7.16-7.27 (m, 1 H) 7.28-7.40 (m, 2 H) 7.64 (s, 1H) 8.18 (d, J=7.93 Hz, 1 H) 8.69 (d, J=11.59 Hz, 1 H);

$^{13}$C NMR (75 MHz, CDCl$_3$) δ 28.0, 51.5, 52.4, 84.1, 113.7, 115.2, 120.0, 122.8, 123.3, 124.6, 126.7, 129.8, 131.2, 134.9, 135.2, 139.0, 149.2, 166.0, 167.0; FT-IR (neat): 1719, 1476, 1373, 1247, 1174, 1154 cm$^{-1}$; HRMS (neg-APCI) calcd for C$_{16}$H$_{14}$O$_4$N$_1$: 384.09283 Found: 384.09284.

(2Z,4E)-methyl 6-(3,4-dichlorophenyl)-6-oxohexa-2,4-dienoate

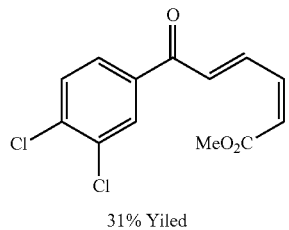

HDAB-034

31% Yiled

A solution of 2-diazo-1-(3,4-dichlorophenyl)ethanone (213 mg, 1 mmol, 1 eq.) in hexanes (10 mL) was added by syringe pump over 2 h (5 mL/hr rate) to a solution of 2-methoxy furan (0.2 mL, 2 mmol, 2 eq.) and Rh$_2$(OAc)$_4$ (5 mg, 0.002 mmol, 0.01 eq.) in hexane (10 mL). The reaction mixture was stirred for an additional 1 h, and then concentrated in vacuo and purified by flash chromatography on silica gel using 9:1 hexane/Et$_2$O as eluant to isolate a pale yellow solid (86 mg, 31% yield).

$^1$H NMR (400 MHz): δ 8.45 (dd, J=11, 15 Hz, 1H), δ 8.01 (d, J=2 Hz, 1 H), δ 7.75 Hz (dd, J=8, 2 Hz, 1H), δ 7.56 (d, J=8 Hz, 1H), δ 7.01 (d, J=15 Hz, 1H), δ 6.76 (t, J=11 Hz, 1H), δ 6.07 (d, J=11 Hz, 1H), δ 3.80 (s, 3H).

(2Z,4E)-methyl 6-(4-bromophenyl)-6-oxohexa-2,4-dienoate

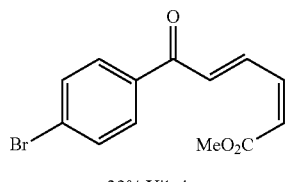

HDAB-035

32% Yiled

A solution of 1-(4-bromophenyl)-2-diazoethanone (223 mg, 1 mmol, 1 eq.) in hexanes (10 mL) was added by syringe pump over 2 h (5 mL/hr rate) to a solution of 2-methoxy furan (0.2 mL, 2 mmol, 2 eq.) and Rh$_2$(OAc)$_4$ (5 mg, 0.002 mmol, 0.01 eq.) in hexane (10 mL). The reaction mixture was stirred for an additional 1 h, and then concentrated in vacuo and purified by flash chromatography on silica gel using 9:1 hexane/Et$_2$O as eluant to isolate a pale yellow solid (94 mg, 32%).

1H NMR (400 MHz): δ 8.44 (dd, 1H, J=15.5, 11.7 Hz), 7.82 (d, 2H, 8.8 Hz), 7.65 (d, 2H, J=8.8 Hz), 7.03 (d, 1H, J=15.5 Hz), 6.78 (app t, 1H, J=11.7 Hz), 6.08 (d, 1H, J=11.7 Hz), 3.80 (s, 3H).

(2E,4Z)-dimethyl 2-(benzo[d][1,3]dioxol-5-yl)hexa-2,4-dienedioate

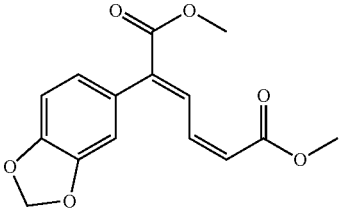

HDAB-036

91% Yield

A solution of methyl 2-(benzo[d][1,3]dioxol-5-yl)-2-diazoacetate (220 mg, 1 mmol, 1 eq.) in hexanes (10 mL) was added by syringe pump over 2 h (5 mL/hr rate) to a solution of 2-methoxy furan (0.2 mL, 2 mmol, 2 eq.) and Rh$_2$(OAc)$_4$ (5 mg, 0.002 mmol, 0.01 eq.) in hexane (10 mL).

The reaction mixture was stirred for an additional 1 h, and then concentrated in vacuo and purified by flash chromatography on silica gel using 9:1 hexane/Et$_2$O as eluant to isolate colorless oily liquid, 263 mg (91%). $^1$H NMR (400 MHz, CDCl$_3$-d) δ 3.80 (s, 3 H) 3.83 (s, 3 H) 5.90 (d, J=11.59 Hz, 1 H) 6.01 (s, 2 H) 6.62-6.71 (m, 2 H) 6.75 (d, J=1.22 Hz, 1 H) 6.84 (d, J=7.93 Hz, 1 H) 8.52 (d, J=11.59 Hz, 1 H); $^{13}$C NMR (75 MHz, CDCl$_3$) δ 51.6, 52.5, 101.4, 101.5, 101.6, 108.0, 110.7, 123.5, 124.5, 127.6, 133.6, 139.1, 139.3, 147.6, 148.0; FT-IR (neat): 1712, 1438, 133, 1195, 1173, 728 cm$^{-1}$; FIRMS (pos-APCI) calcd for C$_{15}$H$_{15}$O$_6$: 291.08631 Found: 291.08638.

(2E,4Z)-dimethyl 2-(2,3-dihydrobenzo[b][1,4]dioxin-6-yl)hexa-2,4-dienedioate

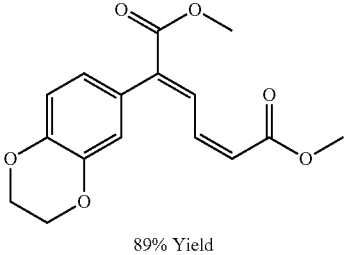

HDAB-037

89% Yield

A solution of methyl 2-diazo-2-(2,3-dihydrobenzo[b][1,4]dioxin-6-yl)acetate (234 mg, 1 mmol, 1 eq.) in hexanes (10 mL) was added by syringe pump over 2 h (5 mL/hr rate) to a solution of 2-methoxy furan (0.2 mL, 2 mmol, 2 eq.) and Rh$_2$(OAc)$_4$ (5 mg, 0.002 mmol, 0.01 eq.) in hexane (10 mL). The reaction mixture was stirred for an additional 1 h, and then concentrated in vacuo. Purified by flash chromatography on silica gel using 9:1 hexane/Et$_2$O as eluant to isolate colorless oily liquid, 270 mg (89%).

$^1$H NMR (400 MHz, CDCl$_3$-d) δ 3.77 (s, 3 H), 3.78 (s, 3 H) 4.26 (s, 4 H) 5.86 (dd, J=11.29, 0.92 Hz, 1 H) 6.62-6.72 (m, 2 H) 6.75 (d, J=1.83 Hz, 1 H) 6.86 (d, J=8.24 Hz, 1 H) 8.47 (d,

J=11.90 Hz, 1 H); $^{13}$C NMR (75 MHz, CDCl$_3$) δ 51.2, 52.1, 63.9, 64.1, 116.5, 119.0, 122.9, 123.4, 126.6, 133.0, 138.6, 139.0, 142.7, 143.7, 165.8, 167.1; FT-IR (neat): 1711, 1506, 1435, 1250, 1173 cm$^{-1}$; HRMS (neg-APCI) calcd for C$_{16}$H$_{16}$O$_6$: 304.09524 Found 304.09564.

(E)-tert-butyl 3-((Z)-4-methoxy-4-oxobut-2-en-1-ylidene)-2-oxoindoline-1-carboxylate

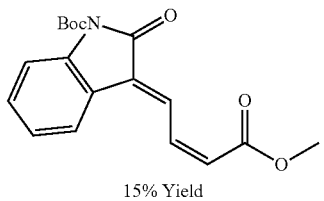

HDAB-038

15% Yield

A solution of tert-butyl 3-diazo-2-oxoindoline-1-carboxylate (259 mg, 1 mmol, 1 eq.) in hexanes (10 mL) was added by syringe pump over 2 h (5 mL/hr rate) to a solution of 2-methoxy furan (0.2 mL, 2 mmol, 2 eq.) and Rh$_2$(OAc)$_4$ (5 mg, 0.002 mmol, 0.01 eq.) in hexane (10 mL). The reaction mixture was stirred for an additional 1 h, and then concentrated in vacuo and purified by flash chromatography on silica gel using 9:1 hexane/Et$_2$O as eluant to isolate colorless oily liquid, 49 mg (15%).

$^1$H NMR (400 MHz, CDCl$_3$-d) δ 1.66 (s, 9 H) 3.80 (s, 3 H) 6.12 (d, J=11.59 Hz, 1 H) 7.12-7.20 (m, 1 H) 7.35 (t, J=7.78 Hz, 1 H) 7.60 (d, J=7.63 Hz, 1 H) 7.83 (d, J=8.24 Hz, 1 H) 8.30-8.42 (m, 1 H) 8.55 (d, J=12.20 Hz, 1 H); $^{13}$C NMR (75 MHz, CDCl$_3$) δ 28.3, 51.7, 84.5, 115.4, 120.7, 123.1, 124.4, 125.1, 129.3, 129.8, 130.9, 137.4, 139.7, 149.3, 165.1, 166.4, 165.1, 166.4; FT-IR (neat): 1725, 1604, 1466, 1351, 1144, 829 cm$^{-1}$; FIRMS (neg-APCI) calcd for C$_{17}$H$_{19}$O$_5$N: 329.12687 Found: 329.12681.

(2Z,4E)-methyl 4-(2-oxoindolin-3-ylidene)but-2-enoate

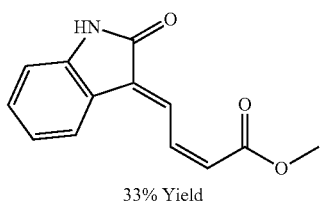

HDAB-039

33% Yield

A solution of 3-diazoindolin-2-one (159 mg, 1 mmol, 1 eq.) in hexanes (10 mL) was added by syringe pump over 2 h (5 mL/hr rate) to a solution of 2-methoxy furan (0.2 mL, 2 mmol, 2 eq.) and Rh$_2$(OAc)$_4$ (5 mg, 0.002 mmol, 0.01 eq.) in hexane (10 mL). The reaction mixture was stirred for an additional 1 h, and then concentrated in vacuo and purified by flash chromatography on silica gel using 9:1 hexane/Et$_2$O as eluant to isolate colorless oily liquid, 75 mg (33%).

$^1$H NMR (400 MHz, CDCl$_3$-d) δ 3.81 (s, 3 H) 6.10 (d, J=11.29 Hz, 1 H) 6.84 (d, J=7.63 Hz, 1 H) 6.97-7.07 (m, 1 H) 7.20-7.30 (m, 2 H) 7.54 (d, J=7.63 Hz, 1 H) 8.15 (br. s., 1 H) 8.34-8.45 (m, 1 H) 8.48-8.56 (m, 1 H); $^{13}$C NMR (75 MHz, CDCl$_3$) δ 51.5, 109.8, 121.2, 122.2, 123.5, 124.1, 129.3, 130.5, 137.4, 141.0, 166.3, 168.7; FT-IR (neat): 3169, 3061, 2921, 1685, 1200, 1179, 742 cm$^{-1}$; HRMS (pos-APCI) calcd for C$_{13}$H$_{12}$O$_3$N: 230.08117 Found: 230.08110.

1.4.3 Synthesis of Chiral Furan Diol

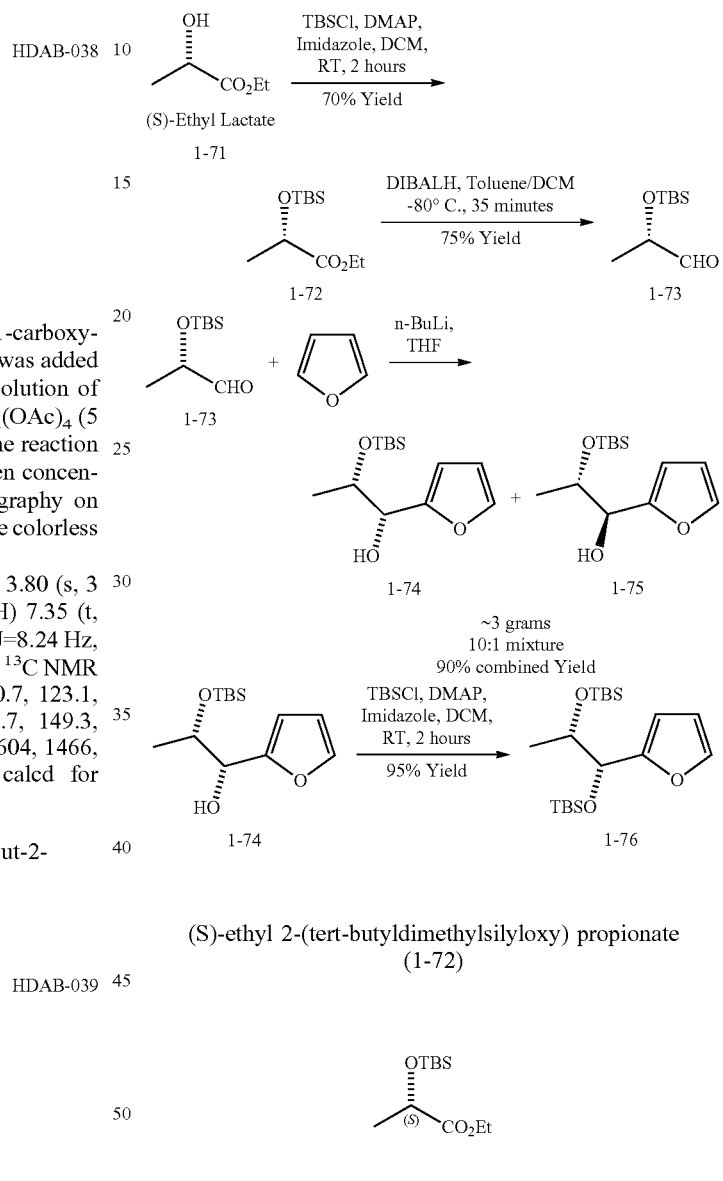

(S)-ethyl 2-(tert-butyldimethylsilyloxy) propionate (1-72)

A solution of ter-butyldimethylsilylchloride (8.29 g, 55 mmol, 1.1 eq.) in dichloromethane (20 mL) was added to a solution of (S)-ethyl lactate (4.18 mL, 50 mmol, 1 eq), imidazole (5.1 g, 75 mmol, 1.5 eq.) and dimethylamino pyridine (183 mg, 1.5 mmol, 0.03 eq.) in dichloromethane (50 mL) at 0° C. The reaction mixture was stirred for overnight, and then added water, extracted with dichloromethane, dried over MgSO$_4$ and concentrated in vacuo and purified by flash chromatography on silica gel using 9:1 hexane/Et$_2$O as eluant to isolate colorless oily liquid, 8.12 g (70%).

$^1$H NMR (500 MHz, CDCl$_3$): δ4.30 (q, 1H, J=7 Hz), 4.22-4.11 (m, 2H), 1.39 (d, 3H, J=7 Hz), 1.27 (t, 3H, J=7 Hz), 0.90 (s, 9H), 0.09 (d, 6H, J=14.5 Hz). See Smith et al., Synthesis, 1996, 652-666.

(S)-2-(tert-butyldimethylsilyloxy) propanal (1-73)

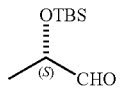

A solution of DIBAL-H (36 mL of 1M solution in toluene) was added to a solution of (S)-ethyl 2-(tert-butyldimethylsilyloxy) propionate (8.12 g, 35 mmol, 1 eq.) in dichloromethane (50 mL) at −78° C. slowly drop wise. The reaction mixture was stirred for 1 hr, and then added water, extracted with dichloromethane, dried over MgSO4 and concentrated in vacuo and purified by flash chromatography on silica gel using 9:1 hexane/Et$_2$O as eluant to isolate colorless oily liquid, 4.9 g (75%).

$^1$H NMR (500 MHz, CDCl$_3$): δ9.61 (s, 1H), 4.11-4.07 (m, 1H), 1.27 (d, 3H, J=7 Hz), 0.91 (s, 9H), 0.10 (d, 6H, J=6 Hz). See Martin et al., Tetrahedron, 1999, 55, 3561-3572.

(1R, 2S)-2-(tert-butyldimethylsilyloxy)-1-(furan-2-yl) propan-1-ol (1-74)

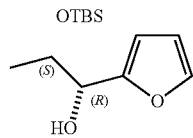

A solution of n-BuLi (16 mL of 2.5 M solution in hexane) was added to the freshly distilled furan (2.7 g, 40 mmol, 2 eq.) dissolved in THF (50 mL) at 0° C. The reaction mixture stirred at 0° C. for 2 hours and then cooled to −78° C. (S)-2-(tert-butyldimethylsilyloxy) propanal (3.7 g, 20 mmol, 1 eq.) was added drop wise at −78° C. and stirred at that temperature for 3 hours. The reaction was quenched with NaHCO$_3$, filtered though celite, extracted with dichloromethane, dried over MgSO$_4$ and concentrated in vacuo and purified the epimeric mixture by flash chromatography on silica gel using 20:1 hexane/Et$_2$O as eluant to isolate colorless oily liquid, 2.7 g (52%).

$^1$H NMR (500 MHz, CDCl$_3$): δ7.36 (s, 1H), 6.33 (d, 1H, J=3 Hz), 6.29 (d, 1H, J=3 Hz), 4.58(s, 1H), 4.11(m, 1H), 2.44 (s, 1H), 1.12 (d, 3H, J=6 Hz), 0.87 (s, 9H), 0.06 (d, 6H, J=22.5 Hz). See Martin et al., Tetrahedron, 1999, 55, 3561-3572.

(5R, 6S)-5-(furan-2-yl)-2,2,3,3,6,8,8,9,9-nonamethyl-4,7-dioxa-3,8-disiladecane (1-76)

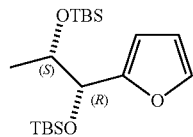

A solution of ter-butyldimethylsilylchloride (331 mg, 2.2 mmol, 1.1 eq.) in dichloromethane (10 mL) was added to a solution of (1R, 2S)-2-(tert-butyldimethylsilyloxy)-1-(furan-2-yl) propan-1-ol (512 mg, 2 mmol, 1 eq.), imidazole (204 mg, 3 mmol, 1.5 eq.) and dimethylamino pyridine (8 mg, 0.06 mmol, 0.03 eq.) in dichloromethane (10 mL) at 0° C. The reaction mixture was stirred for overnight, and then added water, extracted with dichloromethane, dried over MgSO$_4$ and concentrated in vacuo and purified by flash chromatography on silica gel using 9:1 hexane/Et$_2$O as eluant to isolate colorless oily liquid, 704 mg (95%).

$^1$H NMR (500 MHz, CDCl$_3$): δ7.3 (s, 1H), 6.29 (d, 1H, J=1.5 Hz), 6.19 (d, 1H, J=3 Hz), 4.3 (d, 1H, J=7 Hz), 4.0-3.9 (m, 1H), 1.22 (d, 3H, J=5.5 Hz), 0.84 (s, 9H), 0.77 (s, 9H), 0.02 (s, 3H), −0.05 (s, 3H), −0.15 (s, 3H), −0.21 (s, 3H). $^{13}$C NMR (300 MHz, CDCl$_3$): δ155.6, 141.0, 110.0, 107.6, 73.9, 71.2, 25.76, 25.74, 20.4, 18.1, 17.9, −4.8, −5.13, −5.15, −5.37. HRMS (EI) m/z calcd for [C$_{19}$H$_{38}$O$_3$Si$_2$]$^+$ 383.1649; Found: 383.1642.

1.4.4 Synthesis of o-Hydroxy Methyl Phenyl Diazoacetate

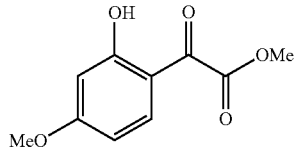 [SMILES: COC(=O)C(=O)c1ccc(OC)cc1O]

Methyl 2-(2-hydroxy-4-methoxyphenyl)-2-oxoethanoate (1-77)

A solution of AlCl$_3$ (6.6 g, 50 mmol, 5 eq.) dissolved in DCE (20 mL) was added through a canula to a solution of 1,3 dimethoxybenzene (1.3 g, 10 mmol, 1 eq.) and methyloxalyl chloride (1.2 g, 10 mmol, 1 eq.) dissolved in DCE (50 mL) at 0° C. The reaction mixture stirred at RT for overnight. The resultant solution was quenched by adding water, extracted twice with dichloromethane, dried over MgSO$^4$ and concentrated in vacuo and purified by flash chromatography on silica gel using 9:1 hexane/Et$_2$O as eluant to isolate colorless oily liquid, 1.9 g (90%).

$^1$H NMR (500 MHz, CDCl$_3$): δ11.6 (s, 1H), 7.62 (d, 1H, J=9 Hz), 6.45 (dd, 1H, J=8.5 Hz), 6.41 (d, 1H, J=2.5 Hz), 3.93 (s, 3H), 3.82 (s, 3H). See Chatterjea, Indian Chem. Soc., 1954, 31, 194-202 and Kraus & Zhang, Org. Chem., 2000, 65, 5644-5646.

Methyl 2-(2-(tert-butyldimethylsilyloxy)-4-methoxyphenyl)-2-oxoethanoate (1-80)

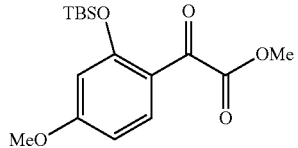 [SMILES: COC(=O)C(=O)c1ccc(OC)cc1O[Si](C)(C)C(C)(C)C]

A solution of ter-butyldimethylsilylchloride (165 mg, 1.1 mmol, 1.1 eq.) in dichloromethane (10 mL) was added to a solution of methyl 2-(2-hydroxy-4-methoxyphenyl)-2-oxoethanoate (210 mg, 1 mmol, 1 eq.), imidazole (102 mg, 1.5 mmol, 1.5 eq.) and dimethylamino pyridine (4 mg, 0.03 mmol, 0.03 eq.) in dichloromethane (10 mL) at 0° C. The reaction mixture was stirred for overnight, and then added water, extracted with dichloromethane, dried over MgSO⁴ and concentrated in vacuo and purified by flash chromatography on silica gel using 9:1 hexane/Et$_2$O as eluant to isolate colorless oily liquid, 251 mg (77%).

$^1$H NMR (500 MHz, CDCl$_3$): δ7.73 (d, 1H, J=8.5 Hz), 6.59-6.56 (dd, 1H, J=2.0 Hz), 6.37 (s, 1H), 3.87 (s, 3H), 3.81 (s, 3H), 0.96 (s, 9H), 0.28 (s, 6H). $^{13}$C NMR (300MHz, CDCl$_3$): δ185.5(C), 165.6(C), 165.0(C), 158.8(C), 133.0 (CH), 118.5(C), 107.6(CH), 105.1(CH), 55.5(CH3), 52.3 (CH3), 25.9(CH3), 18.8(C), −3.87(CH3). Anal. Calcd. for C$_{14}$H$_{12}$Cl$_2$O$_4$: C, 59.23; H, 7.46. Found: C, 59.06; H, 7.46.

1.4.5 Synthesis of Diazoketones

Representative Procedure for the Synthesis of Aryl Diazo Ketones

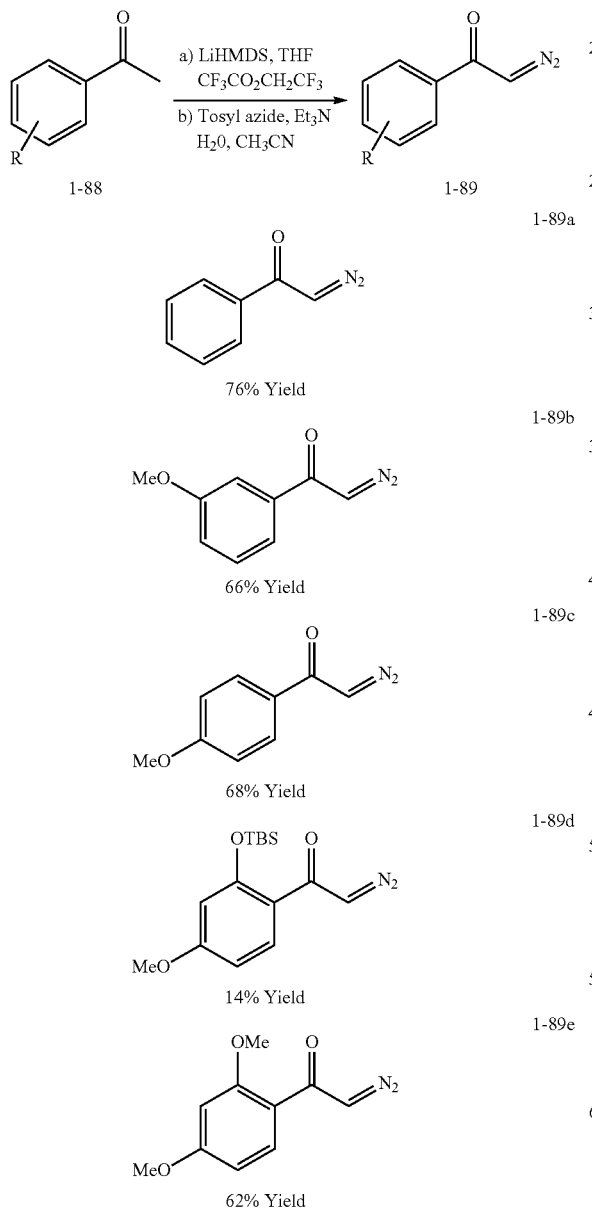

In a flame dried round bottom flask, THF (20 mL) was added. 1,1,1,3,3,3 hexamethyldisilazane (1.7754 gms, 11 mmoles, 1.1 eq) was added to the cooled THF solution. n-BuLi (2.5 M solution in hexane) at 0° C. The resultant mixture was cooled to −78° C. and 3-methoxy acetophenone (1.5018 gms, 10 mmoles, 1 eq.) dissolved in 10 mL of THF was added slowly using syringe pump at −78° C. The reaction mixture is stirred at RT for 3 hours and then trifluoroethyltrifluoroacetate (2.16 gms, 11 mmoles, 1.1 eq.) was added at a time. The resultant yellow reaction mixture was stirred at RT for overnight. The reaction mixture was poured in to a separation funnel having ethyl ether and 5% HCl. Extracted twice, combined organic layers washed with brain, dried over magnesium sulfate and then concentrated in vacuo. The crude mixture was taken into next step without further purification. The resultant yellow solid was dissolved in acetonitrile; water, Et3N and Tosyl azide were added sequentially. Reaction mixture stirred at RT for few hours. Reaction mixture poured into mixture of ethyl ether and 5% NaOH, extracted twice, combined organic layers were washed with brain, dried over magnesium sulfate and then concentrated in vacuo and purified by flash chromatography on silica gel using 9:1 hexane/Et$_2$O as eluant to isolate yellow crystalline solid, 1.164 gms. (66% Yield).

2-Diazo-1-(3-methoxyphenyl) ethanone (1-89b)

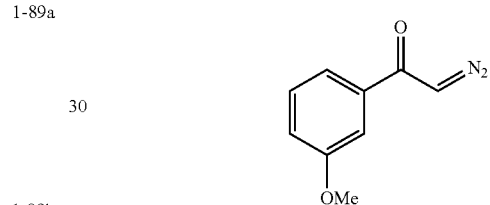

$^1$H NMR (500 MHz, CDCl$_3$): δ7.32 (s, 1H), 7.26 (m, 2H), 7.03 (m, 1H), 6.00 (s, 1H), 3.76 (s, 3H). 13C NMR (300 MHz, CDCl3): δ186.6, 160.3, 138.4, 130.1, 119.4, 119.2, 112.0, 55.79, 54.85.

2-Diazo-1-(4-methoxyphenyl) ethanone (1-89c)

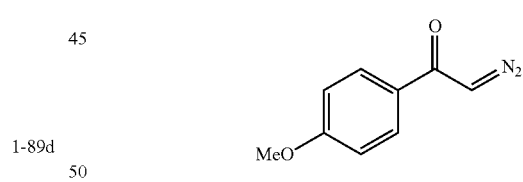

$^1$H NMR (500 MHz, CDCl$_3$): δ7.69 (d, 2H, J=8.8 Hz), 6.86 (d, 2H, J=8.8 Hz), 5.92 (s, 1H), 3.79 (s, 3H). 13C NMR (300 MHz, CDCl3): δ185.7(C), 163.7(C), 129.8(C), 129.2 (CH), 114.2(CH), 55.89(CH3), 53.97(CH).

2-Diazo-1-(2,4-dimethoxyphenyl) ethanone (1-89e)

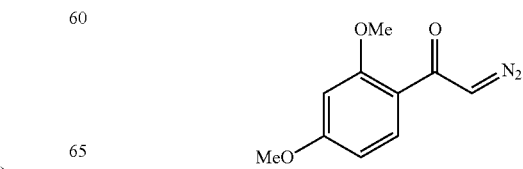

$^1$H NMR (500 MHz, CDCl$_3$): δ7.88 (d, 1H, J=8 Hz), 6.47 (d, 1H, J=8 Hz), 6.35 (s, 1H), 6.29(s, 1H), 3.78 (s, 3H), 3.75 (s, 3H).

1-(2-(tert-butyldimethylsilyloxy)-4-methoxyphenyl) ethanone (Precursor for 1-89d)

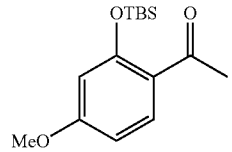

This compound was synthesized from corresponding o-hydroxy, p-methoxy acetophenone. A solution of ter-butyldimethylsilylchloride (5 g, 33 mmol, 1.1 eq.) in dichloromethane (10 mL) was added to a solution of 4-methoxy 2-hydroxy acetophenone (5 g, 30 mmol, 1 eq.), triethylamine (6.2 mL, 45 mmol, 1.5 eq.) and dimethylamino pyridine (03 g, 3 mmol, 0.1 eq.) in dichloromethane (40 mL) at 0° C. The reaction mixture was stirred for overnight, and then added water, extracted with dichloromethane, dried over MgSO$_4$ and concentrated in vacuo, and purified by flash chromatography on silica gel using 9:1 hexane/Et$_2$O as eluant to isolate colorless oily liquid, 6.26 g (75%).

$^1$H NMR (500 MHz, CDCl$_3$): δ7.63 (d, 1H, J=9 Hz), 6.46 (d, 1H, J=8.5 Hz), 6.30 (s, 1H), 3.72(s, 3H), 2.49 (s, 3H), 0.94(s, 9H), 0.23(s, 6H).

Cytotoxicity Assay

The assay consists of treatment of cells with the synthetic compounds (a range of concentrations) and subsequent quantification of the cells by staining with methylene blue and measuring optical density of the resulting colored solution. The measured optical densities are normalized to a vehicle-control and the normalized values are used to determine IC$_{50}$ values for a given compound using SigmaPlot software, Systat Software, Inc., San Jose, Calif. Cells were seeded in 96-well plate at 2-5,000 cells/well in 100 μl. Next day cells were treated with HDAB compounds. Stocks of compounds (10 mM) were prepared by dissolving in DMSO. Consecutive dilutions ranging 10 nM-100 μM concentrations were prepared as 2× solutions in media, and 100 μl solutions were added to cells for treatment. DMSO was used as a vehicle control. Cells were incubated with compounds for 48 hours at 37° C. in a CO$_2$-incubator. For cell staining, media was removed and cells were fixed and stained with 0.5% Methylene blue in water/methanol (50:50) solution for 1 hour at room temperature (RT). After extensive rinsing in ddH$_2$O the plates were dried over-night. Cells were solubilized in 100 μl/well of 1% SDS in PBS for 10 minutes at RT, the absorbance at 650 nm (methylene-blue absorbance) and 540 nm (background) was read with a SpectraMax fluorimeter and the difference Abs650-Abs540 was calculated. The IC$_{50}$ values for the compounds in MDA-MB-231 cells are shown in Table 1.

TABLE 1

Cytotoxicity in breast carcinoma MDA-MB-231 cells

| Compound | IC50, uM |
|---|---|
| HDAB001 | 4.62 |
| HDAB006 | 14.23 |

TABLE 1-continued

Cytotoxicity in breast carcinoma MDA-MB-231 cells

| Compound | IC50, uM |
|---|---|
| HDAB007 | 6.34 |
| HDAB010 | 4.13 |
| HDAB011 | 4.96 |
| HDAB015 | 1.57 |
| HDAB022 | 2.16 |
| HDAB023 | 36.48 |
| HDAB025 | 14.68 |
| HDAB026 | >100 |
| HDAB027 | >100 |
| HCAB028 | 4.37 |
| HDAB029 | 48.27 |
| HDAB031 | >100 |
| HDAB032 | >50 |
| HDAB033 | >50 |
| HDAB034 | 4.98 |
| HDAB035 | 8.40 |
| HDAB036 | 18.00 |
| HDAB037 | 22.00 |
| HDAB038 | 21.23 |
| HDAB039 | >45 |

Cytotoxicity of HDAB001 in Non-Tumor and Carcinoma Cells

Figure 1B:
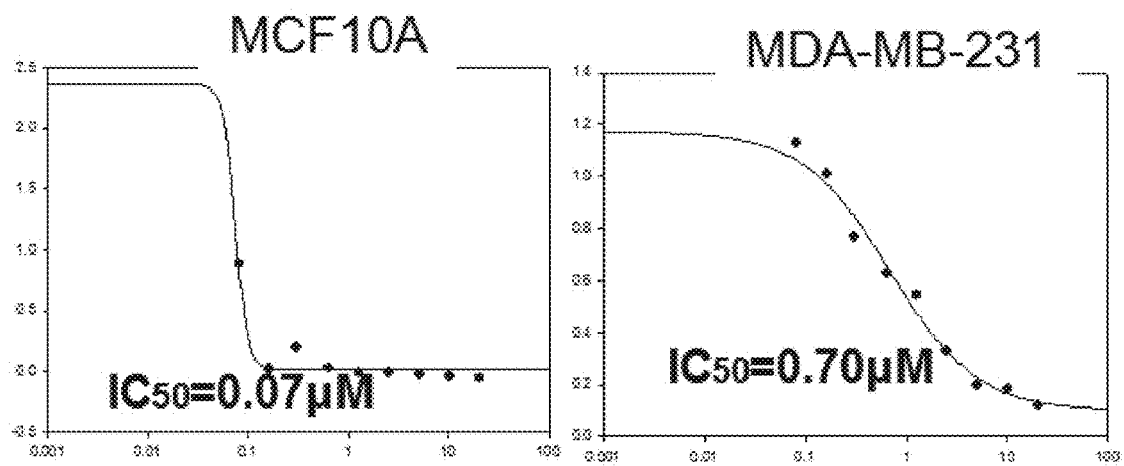
FIG. 1B shows data on the cytotoxicity of doxorubicin.

Assays were carried out with a panel of breast, prostate and lung carcinoma and non-tumor cell lines with HDAB-001. Three ER-positive cell lines showed sub-micromolar IC$_{50}$ values (0.3-0.75 μM), two ER/HER2-positive lines exhibited low micromolar IC$_{50}$ (1-1.5 μM), triple-negative MDA-MB-231 cells were inhibited at IC$_{50}$=3.7 μM (FIG. 1A and Table 2). HDAB001 also inhibited mouse carcinoma cell line 4T1 (from BALB/c mice) at 0.53 μM. Non-tumor MCF10A (ER-, PR-) and MCF12A (ER+) cells were inhibited with IC$_{50}$ nearly 20-fold greater than tumor cells (48 μM and >100 μM, respectively). In contrast, two clinical chemotherapeutic drugs Doxorubicin and 5-FluroroUricil (5FU) were 3-10-fold more toxic to non-tumor MCF10A than to breast cancer MDA-MB-231 cells (see FIG. 1B and for 5FU, IC$_{50}$ values were 1.80 μM and 5.70 μM, respectively). The selectivity trend for HDAB001 was further validated in a set of prostate carcinoma and non-tumor epithelial cell lines. Together this data indicates that HDAB001 preferentially inhibits tumor cells compare to non-tumor cells, with at least twenty-fold selectivity.

TABLE 2

Cytotoxicity of HDAB001 in Prostate Carcinoma Cell lines

| Cell Line | AR-status | IC50, μM | Tumorigenicity |
|---|---|---|---|
| PC3 | neg | 2.3 | Metastatic |
| LNCaP | pos | 2.1 | Tumor |
| LNCaP-C4-2 | pos, ind | 0.5 | metastatic |
| RWPE-1 | pos | 40.1 | non-tumor |
| RWPE-2 | pos | 2.4 | tumor, metastatic |

Cytotoxicity of HDAB001 Compared to 5Z-7-oxozeanol, U0126 and AG1478 Compounds.

Figure 2:
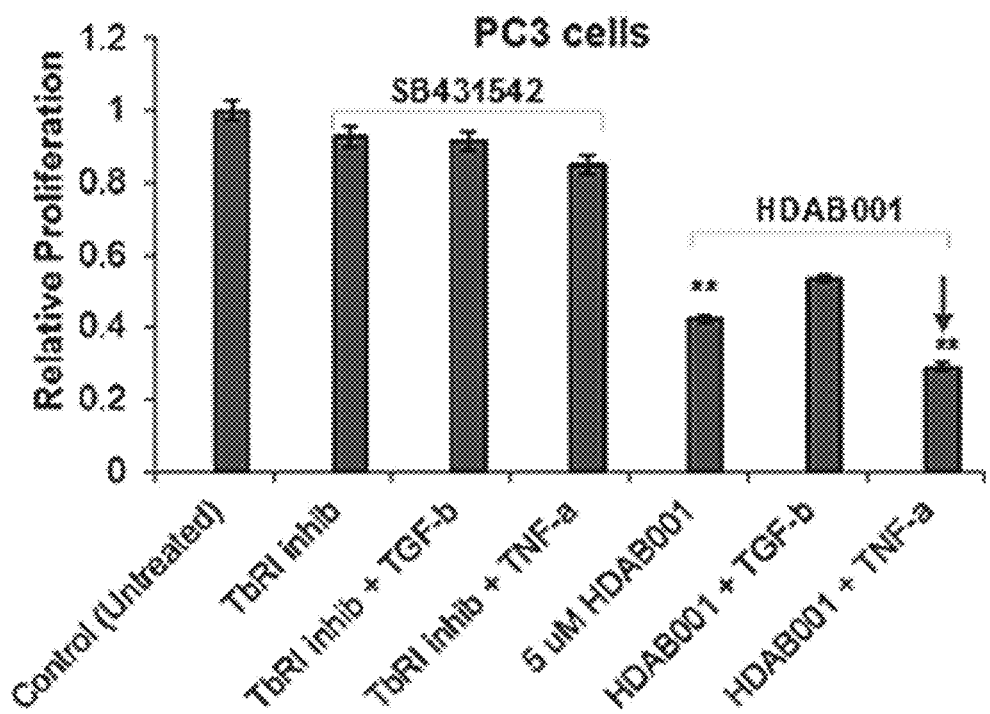
FIG. 2 shows data on the proliferation of prostate PC3 cancer cells 48 hrs incubation in the presence of TGF-β (5 ng/ml) or TNFα (10 ng/ml), and kinase inhibitors 5 μM U0126, 10 μM 1478, 5 μM 5Z-7-oxozeanol, 5 μM HDAB001, 5 μM SB431542.

The response of prostate cancer cells (PC3, FIG. 2) and breast cancer MDA-MB-231 cells to HDAB001 was compared with responses to known kinase inhibitors, including 5Z-7-oxozeanol, a selective inhibitor of TAK1; U0126, a selective MEK inhibitor; AG1478, a selective EGFR inhibitor; SB431542, TGFBR1 inhibitor. The tumor cell growth was markedly inhibited by TAK1 inhibitors HDAB001 or 5Z-7-oxozeanol, while tumor cells are less sensitive to MEK inhibitor and are resistant to an EGFR and TGFBR inhibitors. The MEK and EGFR inhibitors effectively blocked inhibition of MEK, EGF and TGF-beta signaling in MDA-MB-231 and MCF10A. Significantly, both HDAB001 and 5Z-7-oxozeanol cooperated with TNFα in repression of tumor cell growth, in agreement with a role of TAK1 in protection against TNFα-induced cell death. Similar results were obtained with mouse mammary carcinoma EMT6 cells. The cytotoxicity studies demonstrate that compound HDAB001, similar to TAK1 inhibitor 5Z-7-oxozeanol, selectively inhibits proliferation of cancer cells compare to non-malignant cells. The results indicate that compound HDAB001 will be more effective if used in combination with TNFα or TNF-related apoptosis-inducing ligand (TRAIL).

Target Selectivity

Figure 3A:
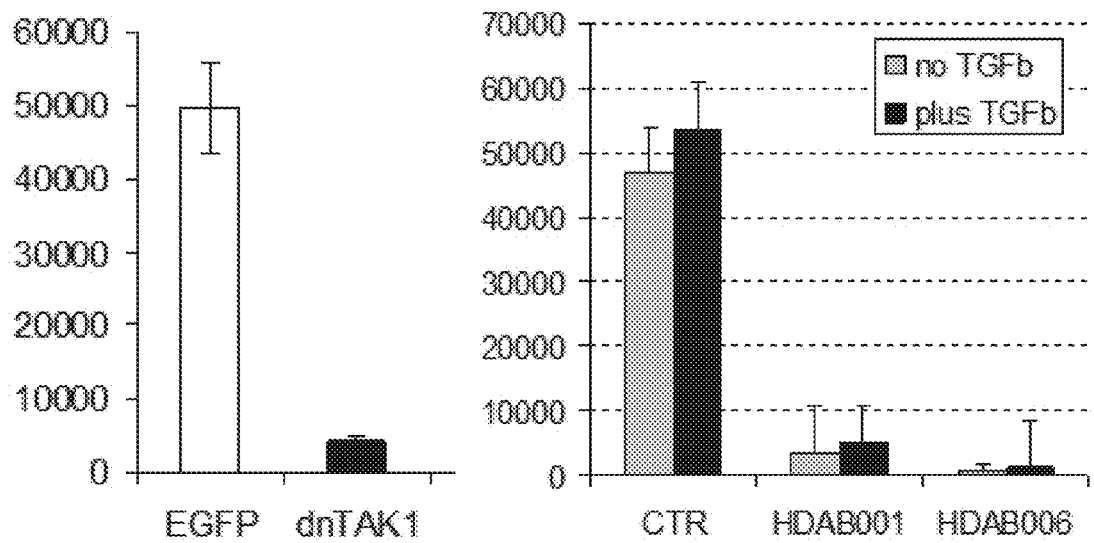
FIGS. 3A-B show data on the luciferase activity of NFkB-Luc and SBE-Luc reporters in MDA-MB-231 control, dnTAK1 or cells treated with HDAB001 and HDAB006, P-values by the ANOVA test.
Figure 3B:
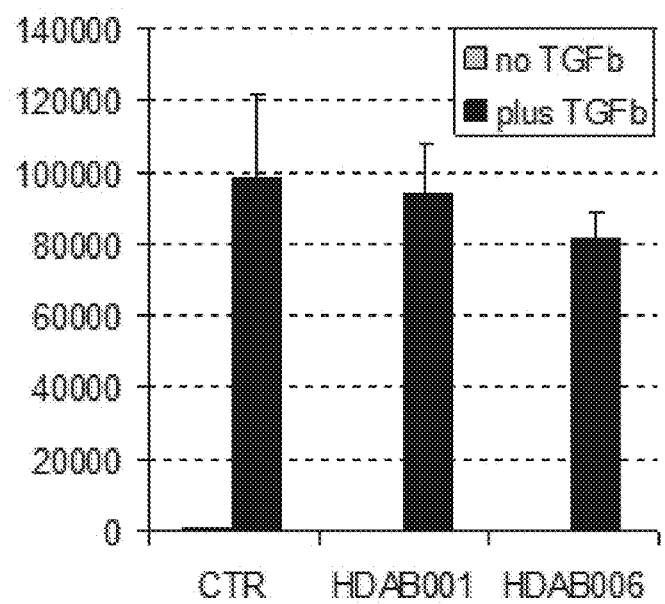
Figure 3C:
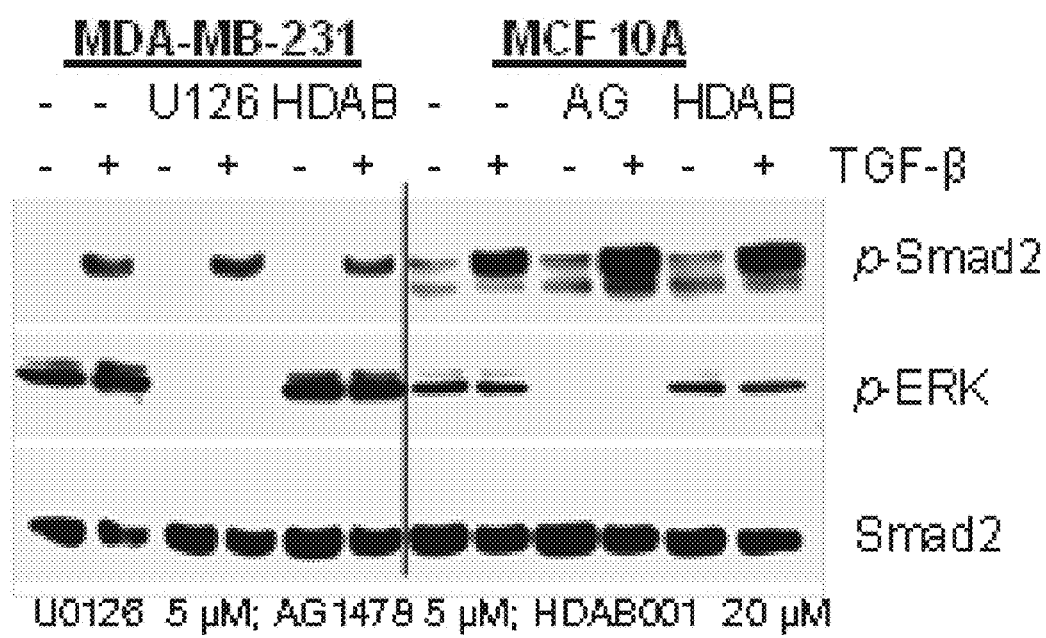
FIG. 3C shows data on MDA-MB-231 and MCF10A cells treated with 2 ng/ml TGFβ1 for 2 hours −/+5 μM U0126, 10 μM AG1478, or 10 μM HDAB001. MEK inhibitor U0126 inhibits phosphorylation of ERK and EGFR inhibitor blocks EGFR-mediated phospho-ERK in MCF10A.

The selectivity of the HDAB001 and HDAB006 compounds was tested in several cell-based assays examining the kinase activity of RAF, MEK, EGFR and TGFBR1. Several known inhibitors of the above kinases were used for control. Two luciferase reporters NF-KB-Luc and SBE-Luc were transfected in MDA-MB-231 cells to assess the effect of compounds on NF-KB and TGF-beta receptor-Smad signaling events. Expression of dnTAK1 inhibited the NF-kB-Luc reporter activity (FIG. 3A) but did not inhibit TGF-beta reporter. See Safina et al., TAK1 is required for TGF-[beta]1-mediated regulation of matrix metalloproteinase-9 and metastasis. Oncogene, 2008, 27, 1198-1207. Compounds HDAB001 and HDAB006 inhibited NF-kB reporter but did not affect TGF-beta reporter (FIG. 3A-B), in agreement with the action of dnTAK1. The kinase activities of TGF-beta receptors type I and type II are required for phosphorylation of Smad2. HDAB001 did not affect phosphorylation of Smad2 and ERK1/2 at the dose inhibiting NF-kB and tumor cell growth (10 μM; IC50=3.7 μM). In control, MEK inhibitor U0126 effectively blocked phosphorylation of ERK (FIG. 3C). TGFBRI inhibitor blocked phosphorylation of Smad2. In non-tumor MCF10A cells, HDAB001 did not affect phosphorylation of ERK in the presence of EGF-mediated signaling, which was blocked by EGFR inhibitor AG1478 (FIG. 3C). Similar results were obtained for HDAB006. This data indicates that compounds HDAB001 and HDAB006 preferentially inhibit TAK1-dependent signaling via NFkB but do not affect the RAF-MEK-ERK signaling axis, EGFR kinase signaling and TGF-BRI/II kinase signaling.

The invention claimed is:

1. A method of treating cancer comprising administering a pharmaceutical composition comprising a compound of formula IC or salt thereof to a subject in need thereof,
   wherein the cancer is selected from breast cancer, prostate cancer, lung cancer, colon cancer, liver cancer, ovarian cancer, cervical cancer, pancreatic cancer, renal cancer, thyroid cancer, melanoma, myeloma, lymphoma, leukemia, and neuroblastoma,
   wherein formula IC is,

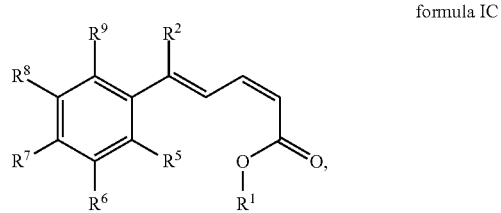

formula IC

R1 is hydrogen, hydroxy, alkyl, alkoxy, carbocyclyl, aryl, or heterocyclyl, wherein R1 is optionally substituted with one or more, the same or different, R10;

R2 is formyl, carboxy, or phosphonate, wherein R2 is optionally substituted with one or more, the same or different, R10;

R5 is hydrogen, alkyl, halogen, nitro, cyano, hydroxy, amino, mercapto, formyl, carboxy, carbamoyl, alkoxy, alkylthio, alkylamino, (alkyl)2amino, alkylsulfinyl, alkylsulfonyl, arylsulfonyl, carbocyclyl, aryl, or heterocyclyl, wherein R5 is optionally substituted with one or more, the same or different, R10;

R6 is hydrogen, alkyl, halogen, nitro, cyano, hydroxy, amino, mercapto, formyl, carboxy, carbamoyl, alkoxy, alkylthio, alkylamino, (alkyl)2amino, alkylsulfinyl, alkylsulfonyl, arylsulfonyl, carbocyclyl, aryl, or heterocyclyl, wherein R6 is optionally substituted with one or more, the same or different, R10;

R7 is hydrogen, alkyl, halogen, nitro, cyano, hydroxy, amino, mercapto, formyl, carboxy, carbamoyl, alkoxy, alkylthio, alkylamino, (alkyl)2amino, alkylsulfinyl, alkylsulfonyl, arylsulfonyl, carbocyclyl, aryl, or heterocyclyl, wherein $R^7$ is optionally substituted with one or more, the same or different, $R^{10}$;

R8 is hydrogen, alkyl, halogen, nitro, cyano, hydroxy, amino, mercapto, formyl, carboxy, carbamoyl, alkoxy, alkylthio, alkylamino, (alkyl)2amino, alkylsulfinyl, alkylsulfonyl, arylsulfonyl, carbocyclyl, aryl, or heterocyclyl, wherein R8 is optionally substituted with one or more, the same or different, R10;

R9 is hydrogen, alkyl, halogen, nitro, cyano, hydroxy, amino, mercapto, formyl, carboxy, carbamoyl, alkoxy, alkylthio, alkylamino, (alkyl)2amino, alkylsulfinyl, alkylsulfonyl, arylsulfonyl, carbocyclyl, aryl, or heterocyclyl, wherein R9 is optionally substituted with one or more, the same or different, R10;

R10 is alkyl, halogen, nitro, cyano, hydroxy, amino, mercapto, formyl, carboxy, carbamoyl, alkoxy, alkylthio, alkylamino, (alkyl)2amino, alkylsulfinyl, alkylsulfonyl, arylsulfonyl, carbocyclyl, aryl, or heterocyclyl, wherein R10 is optionally substituted with one or more, the same or different, R11;

R11 is alkyl, halogen, nitro, cyano, hydroxy, amino, mercapto, formyl, carboxy, carbamoyl, alkoxy, alkylthio, alkylamino, (alkyl)2amino, alkylsulfinyl, alkylsulfonyl, arylsulfonyl, carbocyclyl, aryl, or heterocyclyl, wherein R11 is optionally substituted with one or more, the same or different, R12;

R12 is alkyl, halogen, nitro, cyano, hydroxy, amino, mercapto, formyl, carboxy, carbamoyl, alkoxy, alkylthio, alkylamino, (alkyl)2amino, alkylsulfinyl, alkylsulfonyl, arylsulfonyl, carbocyclyl, aryl, or heterocyclyl, wherein R12 is optionally substituted with one or more, the same or different, R13; and R13 is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethyl sulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

2. The method of claim 1, wherein the compound is selected from:
- (2Z,4Z)-dimethyl 2-(3,4-dichlorophenyl)hexa-2,4-dienedioate,
- (2Z,4Z)-dimethyl 2-(4-bromophenyl)hexa-2,4-dienedioate,
- (2Z,4Z)-dimethyl 2-(4-iodophenyl)hexa-2,4-dienedioate, and
- (2Z,4Z)-dimethyl 2-(4-nitrophenyl)hexa-2,4-dienedioate.

3. The method of claim 1, wherein the subject is diagnosed with a tumor or malignant tumors derived from epithelial cells.

4. The method of claim 1, further comprising administering the compound of formula IC or salt thereof in combination with an additional active agents.

5. The method of claim 4, wherein the additional active agent is a chemotherapy agent.

6. The method of claim 5, wherein the chemotherapy agent is cis-platin or carboplatin.

7. The method of claim 5, wherein the chemotherapy agent is cyclophosphamide.

8. The method of claim 5, wherein the chemotherapy agent is doxorubicin.

9. The method of claim 5, wherein the chemotherapy agent is epirubicin.

10. The method of claim 5, wherein the chemotherapy agent is methotrexate.

11. The method of claim 5, wherein the chemotherapy agent is taxol or taxotere.

12. The method of claim 5, wherein the chemotherapy agent is 5-fluorouracil or tegafur.

13. The method of claim 5, wherein the chemotherapy agent is trastuzumab.

14. The method of claim 5, wherein the chemotherapy agent is gemcitabine.

15. The method of claim 5, wherein the chemotherapy agent is vinorelbine.

16. The method of claim 5, wherein the chemotherapy agent is tamoxifen.

17. The method of claim 5, wherein the chemotherapy agent is imatinib.

* * * * *